(12) United States Patent
Quinn

(10) Patent No.: US 9,990,464 B1
(45) Date of Patent: Jun. 5, 2018

(54) LABEL-FREE BIOMOLECULAR INTERACTION ANALYSIS USING A RAPID ANALYTE DISPERSION INJECTION METHOD

(71) Applicant: SENSIQ TECHNOLOGIES, INC., Oklahoma City, OK (US)

(72) Inventor: John Gerard Quinn, Edmond, OK (US)

(73) Assignee: Pall Corporation, Port Washington, NY (US)

( * ) Notice: Subject to any disclaimer, the term of this patent is extended or adjusted under 35 U.S.C. 154(b) by 1143 days.

(21) Appl. No.: 14/049,863

(22) Filed: Oct. 9, 2013

Related U.S. Application Data

(60) Provisional application No. 61/711,678, filed on Oct. 9, 2012.

(51) Int. Cl.
  *C12M 1/34* (2006.01)
  *G06F 19/12* (2011.01)
  (Continued)

(52) U.S. Cl.
  CPC ............. *G06F 19/12* (2013.01); *G01N 21/55* (2013.01); *G01N 21/553* (2013.01); *G01N 33/53* (2013.01);
  (Continued)

(58) Field of Classification Search
  CPC ........ G01N 35/085; G01N 1/38; G01N 13/00; G01N 15/1429; G01N 2021/058;
  (Continued)

(56) References Cited

U.S. PATENT DOCUMENTS

| 5,519,635 A | 5/1996 | Miyake et al. |
| 5,753,518 A | 5/1998 | Karlsson |

(Continued)

FOREIGN PATENT DOCUMENTS

| AU | 2004245883 | 12/2004 |
| EP | 1775591 | 4/2007 |

(Continued)

OTHER PUBLICATIONS

Karlsson, Robert et al.; Analyzing a Kinetic Titration Series Using Affinity Biosensors; Anal. Biochem. 349 (2006) 136-147.

(Continued)

*Primary Examiner* — Erik B Crawford
(74) *Attorney, Agent, or Firm* — McAfee & Taft

(57) ABSTRACT

Dispersion injection methods for determining biomolecular interaction parameters in label-free biosensing systems are provided. The methods generally relate to the use of a single analyte injection that generates a smoothly-varying concentration gradient via dispersion en route to a sensing region possessing an immobilized binding partner. The present method incorporates the use of an internal standard which provides a reference as to the dispersion conditions present which can then be used to calculate an effective diffusion coefficient for the analyte of interest based on a universal calibration function. The effective diffusion coefficient can then be incorporated into the appropriate dispersion model to provide a calibrated dispersion model. The calibrated dispersion model can then be incorporated into the desired interaction model to provide a reliable representation of the analyte concentration at the sensing region at any time during the injection. The use of the internal standard and universal calibration function permit use of a wide range of injection conditions which may not otherwise be consistent with a particular dispersion model. Thus, the present meth- (Continued)

ods allow for higher flow rates and lower sample volumes thereby increasing assay speed and decreasing sample consumption.

13 Claims, 11 Drawing Sheets

(51) Int. Cl.
| | |
|---|---|
| G01N 33/557 | (2006.01) |
| G01N 35/08 | (2006.01) |
| G01N 33/53 | (2006.01) |
| G01N 21/55 | (2014.01) |
| G01N 21/552 | (2014.01) |
| G01N 35/10 | (2006.01) |
| G01N 21/05 | (2006.01) |

(52) U.S. Cl.
CPC .......... *G01N 33/557* (2013.01); *G01N 35/08* (2013.01); *G01N 35/085* (2013.01); *G01N 35/1097* (2013.01); *B01L 2300/0636* (2013.01); *G01N 2021/058* (2013.01)

(58) Field of Classification Search
CPC .......... G01N 2500/02; B01L 3/502776; Y10T 436/117497; B01J 2219/00995
See application file for complete search history.

(56) References Cited

U.S. PATENT DOCUMENTS

| | | | |
|---|---|---|---|
| 5,942,093 | A | 8/1999 | Rakestraw et al. |
| 6,004,515 | A | 12/1999 | Parce et al. |
| 6,149,870 | A | 11/2000 | Parce et al. |
| 6,475,441 | B1 | 11/2002 | Parce et al. |
| 6,541,213 | B1 | 4/2003 | Weigl et al. |
| 7,373,255 | B2 | 5/2008 | Karlsson et al. |
| 7,642,058 | B2 | 1/2010 | Andersson et al. |
| 7,925,448 | B2 | 4/2011 | Karlsson |
| 8,321,152 | B2 | 11/2012 | Karlsson et al. |
| 2001/0027949 | A1 | 10/2001 | Safir et al. |
| 2001/0042712 | A1 | 11/2001 | Battrell et al. |
| 2002/0113095 | A1 | 8/2002 | Jeon et al. |
| 2003/0095897 | A1 | 5/2003 | Grate et al. |
| 2003/0143565 | A1 | 7/2003 | Trutnau |
| 2003/0214304 | A1 | 11/2003 | Karinka et al. |
| 2004/0005585 | A1 | 1/2004 | Shipwash |
| 2004/0258571 | A1 | 12/2004 | Lee et al. |
| 2005/0089890 | A1 | 4/2005 | Cubicciotti |
| 2005/0106742 | A1 | 5/2005 | Wahl |
| 2005/0255000 | A1 | 11/2005 | Yamamoto et al. |
| 2006/0068412 | A1 | 3/2006 | Tang |
| 2007/0084940 | A1 | 4/2007 | Vafai et al. |
| 2007/0172954 | A1 | 7/2007 | Ismagilov et al. |
| 2007/0178015 | A1 | 8/2007 | Schaedlich et al. |
| 2007/0183928 | A1 | 8/2007 | Neyer et al. |
| 2007/0184456 | A1 | 8/2007 | Chee et al. |
| 2008/0019866 | A1 | 1/2008 | Paek et al. |
| 2008/0153169 | A1 | 6/2008 | Hirata et al. |
| 2009/0044619 | A1 | 2/2009 | Fiering et al. |
| 2009/0263285 | A1 | 10/2009 | Malmqvist et al. |
| 2010/0196205 | A1 | 8/2010 | Quinn |
| 2013/0065251 | A1 | 3/2013 | Karlsson et al. |

FOREIGN PATENT DOCUMENTS

| | | |
|---|---|---|
| EP | 1946830 | 7/2008 |
| JP | 2006508477 | 11/2006 |
| WO | WO1996114934 | 5/1996 |
| WO | WO1998156505 | 12/1998 |
| WO | WO2004109284 | 12/2004 |
| WO | WO2004109295 | 12/2004 |
| WO | WO2005118139 | 12/2005 |
| WO | WO2007021756 | 2/2007 |
| WO | WO2009025680 | 2/2009 |
| WO | WO20111088247 | 7/2011 |
| WO | WO2012087840 | 6/2012 |

OTHER PUBLICATIONS

Quinn, John G.; Evaluation of Taylor Dispensing injections: Determining Kinetic/Affinity Interaction Constants and Diffusion Coefficients in Label-Free Biosensing; Anal. Biochem. 421 (2012) 401-410.

Mary L Shank-Retzlaff et al.; Analyte Gradient-Surface Plasmon Resonance: A One-Step Method for Determining Kinetic Rates and Macromolecular Binding Affinities; Anal. Chem. 2000, 72, 4212-4220.

Robert Karlsson; Affinity Analysis of Non-Steady-State Data Obtained Under Mass Transport Limited Conditions Using BIAcore TEchnology; J. Mol. Recognit. 1999: 12:285-292.

Robert Karlsson; Real-Time Competitive Kinetic Analysis of Interactions Between Low-Molecular-Weight Ligands in Solution and Surface-Immobilized Receptors; Anal. Biochem. 221, 142-151 (1994).

Harvey J. Motulsky et al.; The Kinetics of Competitive Radioligand Binding Predicted by the Law of Mass Action; Molecular Pharmacology, 25:1-9.

Peter Schuck et al.; Determination of Binding Constants by Equilibrium Titration with Circulating Sample in a Surface Plasmon Resonance Biosensor; Anal. Biochem. 265,79-91 (1998), Article AB982872.

Joydeep Lahiri et al.; A Strategy for the Generation of Surfaces Presenting Ligands for Studies of Binding Based on an Active Ester as a Common Reactive Intermediate: A Surface Plasmon Resonance Study; Anal. Chem. 1999,71, 777-790.

Lars Nieba et al.; Competition BIAcore for Measuring True Affinities; Large Differences from Values Determined from Binding Kinetics; Anal. Biochem. 234, 144-165 (1996).

Yijun Tang et al.; Nonregeneration Protocol for Surface Plasmon Resonance: Study of High-Affinity Interaction with High-Density Biosensors; Anal. Chem. 2006, 78, 1841-1848.

Rich, Rebecca L. etal.; Biosensor-based fragment screening using FastStep injections; Analytical Biochemistry 407 (2010) pp. 270-277.

Quinn, John; Compound Titrations using OneStep A Practical Tool for label-free screening; Presentation and materials presented in Sep. 2012; 39 pages.

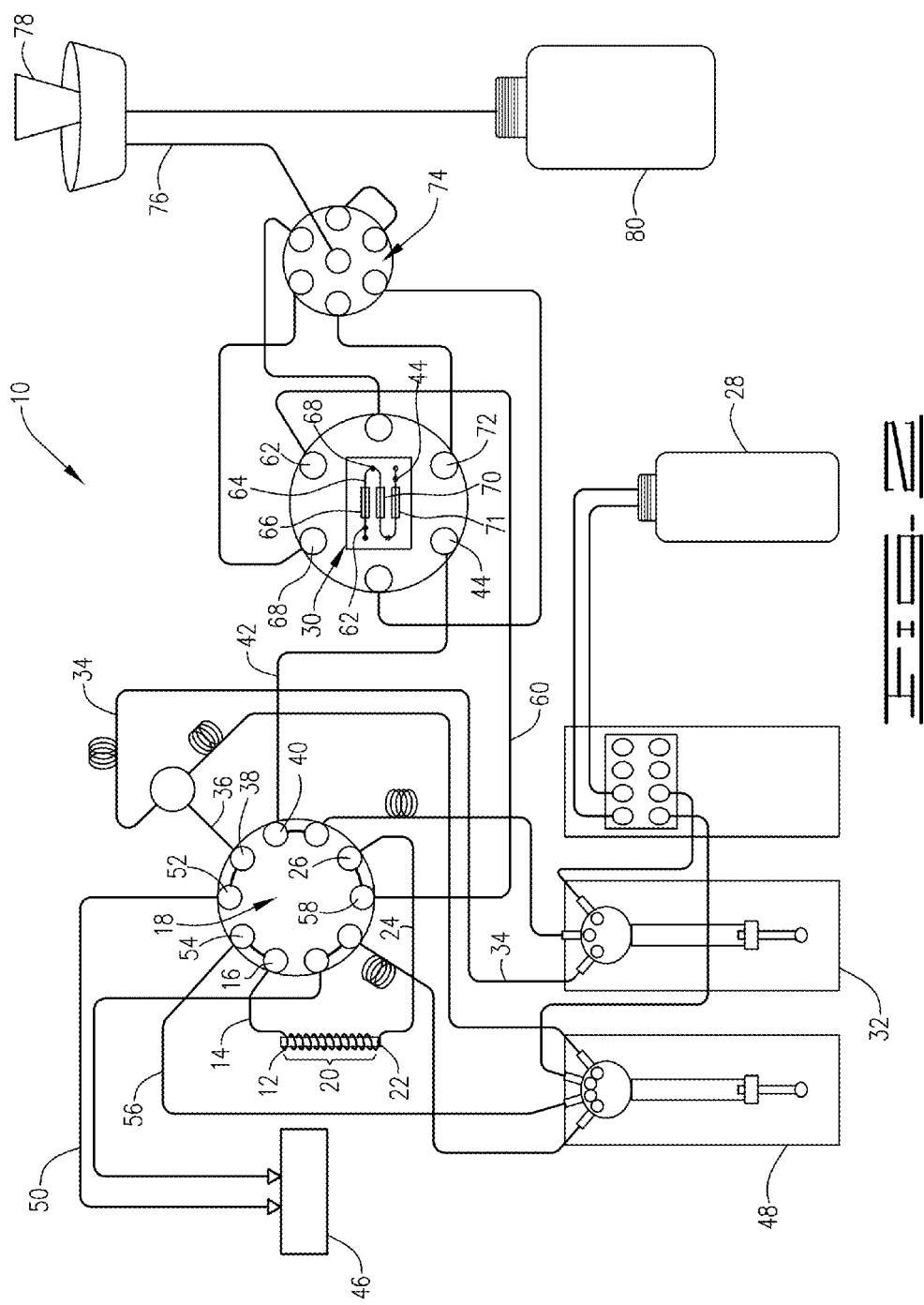

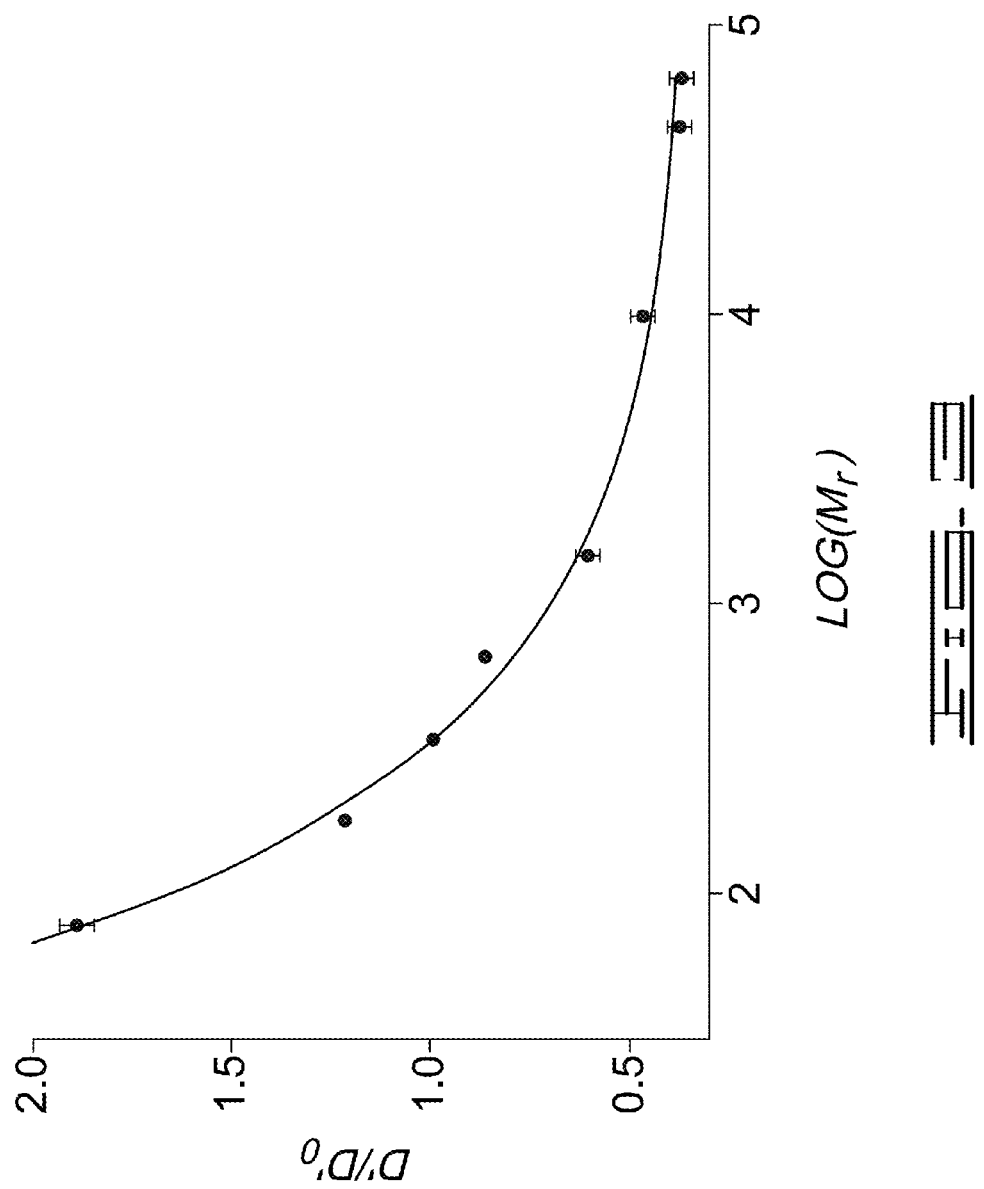

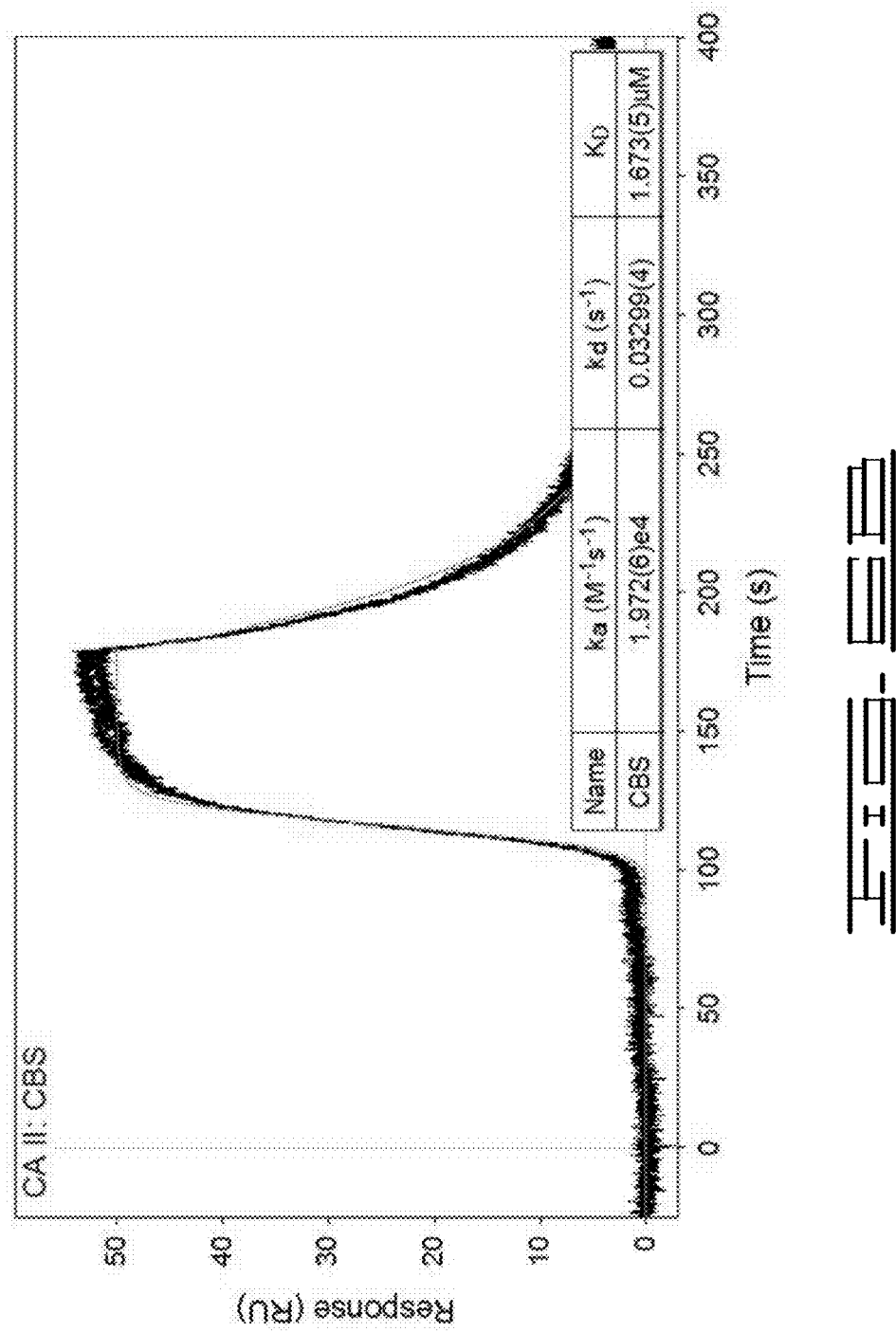

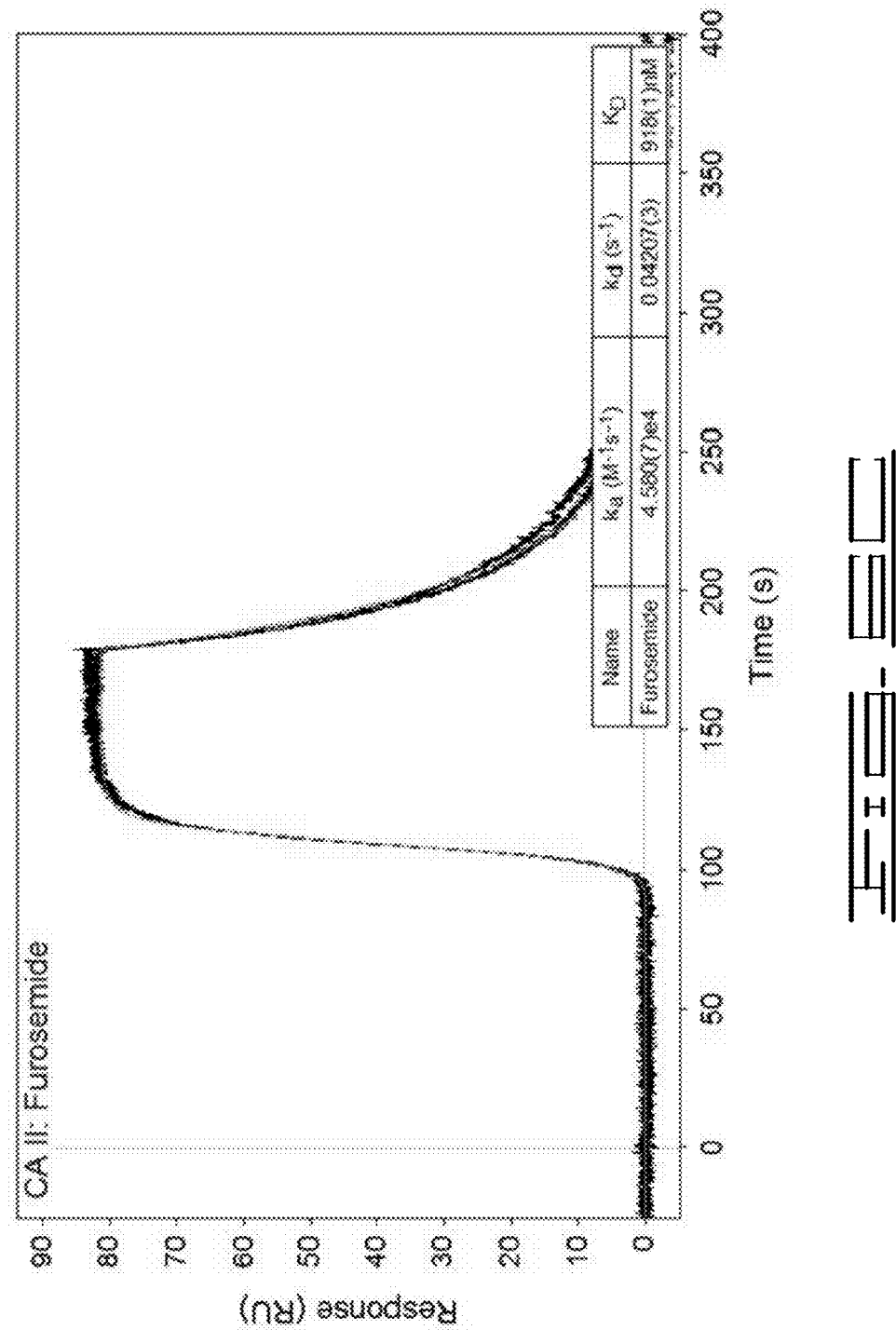

LABEL-FREE BIOMOLECULAR INTERACTION ANALYSIS USING A RAPID ANALYTE DISPERSION INJECTION METHOD

CROSS REFERENCE TO RELATED APPLICATIONS

This application claims the benefit of U.S. Provisional Application No. 61/711,678 filed Oct. 9, 2012.

BACKGROUND

Biosensors are commonly used to perform kinetic studies of complex molecular interactions such as those between drug-target, hormone-receptor, enzyme-substrate and antigen-antibody. The biosensors are typically in a flow injection-based fluidic system wherein one or more sensing regions are housed within a flow cell conduit of the fluidic system. The fluidic system further includes one or more flow channel conduits that direct fluid flow to the sensing regions in the flow cell conduit. The sensing region provides surfaces that support immobilized molecules referred to generally as "ligands." The ligands are potential binding partners for molecules known as "analytes" which are present in fluids that are directed to the sensing region of the flow cell conduit via the flow channel conduit. Typically one member of an affinity pair, the ligand, is immobilized onto a surface in the sensing region while the second member, the analyte, is exposed to this ligand-coated surface for sufficient time to form analyte-ligand complexes at the sensing region. The accumulation of the resulting affinity complexes at the sensing region is detected by a label-free detection method selected from the group consisting of evanescent filed-based optical refractometers, surface plasmon resonance (SPR), optical interferometers, waveguides, diffraction gratings, photonic crystal waveguide arrays, and gravimetric microbalances based on frequency dampening of piezoelectric substrates. The biosensor response is then plotted in real-time and is referred to as a response curve or binding response curve. In order to accurately determine the affinity complex interaction parameters (binding affinity constants, association constants, dissociation constants, diffusion coefficients, etc), the ligand is generally exposed to multiple analyte concentrations.

In WO2012/087840 A1, we described an injection method that permitted a continuum of smoothly changing concentration to be tested through a single injection of sample having a single, starting analyte concentration. In this method, the multiple analyte concentrations are generated en route to the flow cell due to the sample undergoing a mathematically-defined dispersion event thereby producing a well-characterized concentration gradient profile. In order to fit within this mathematical model, the physical injection conditions must be performed in accordance with certain rules relative to, for example, tube length, tube diameter, and flow rate. In one embodiment, Taylor's theory of dispersion provides the basis for the mathematically-defined dispersion event such that the physical injection conditions must be consistent with and comply with the assumptions and limits defined by Taylor dispersion theory. Not only did this method allow for an accurate determination of analyte concentration at any injection time (a feature not present in the prior art single injection methods utilizing uncharacterized concentration gradients), it also provided the ability to determine the diffusion coefficient of the analyte. In more practical terms, the previous dispersion method provides significantly greater throughput in terms of sample number and faster run times, and also significantly extends biophysical characterization in a label-free biosensor.

There are a few limitations on the previous dispersion method. First, the physical conditions under which the injection can occur are limited to those that comply with dispersion model utilized. Under Taylor's model, the flow rate must be low relative to the volume and diameter of the flow channel and can't exceed certain levels without producing a dispersion event that is not consistent with Taylor theory. For practical purposes, the low flow rate equates to a longer injection time thereby decreasing throughput. Thus, an improvement to the method that permits the use of higher flow rates while not departing from the Taylor model is desired.

Second, the previous dispersion method did not account for analyte interactions with the tubing wall en route to the flow cell. When present, these interactions reduce the average velocity of the analyte population relative to the solvent (liquid carrying the analyte) front thereby effecting the residence time of the analyte. By not accounting for this retention time, the dispersion model fails to accurately reflect the gradient profile as the injection progresses. Furthermore, the retention of analyte at the wall can provide added functionality such as chromatographic separation and significant differentiation over existing technology. The improved dispersion method described herein addresses these concerns and provides added functionality.

SUMMARY

A method for calibrating a dispersion model for use in determining interaction parameters between an analyte and a ligand in a label-free biosensor system is provided. The method includes calculating a reference diffusion coefficient for a reference material by fitting a standard curve to a dispersion model which includes an apparent diffusion coefficient term. The standard curve is generated by measuring the bulk refractive index response elicited by the reference material. In one instance, the reference material is sucrose, however, a compound having a molecular weight that is an average of the molecular weight range of the analytes being tested can be used. An effective diffusion coefficient for the analyte of interest can be determined by multiplying the reference diffusion coefficient by a calibration function, wherein a variable in calibration function is the molecular weight of the analyte. The effective diffusion coefficient is then incorporated into the dispersion model to provide the apparent diffusion coefficient term thereby generating the calibrated dispersion model.

A computer software program for performing the calibration methods is also provided. The computer software program uses the equations provided herein to calibrate the dispersion model in accordance with the methods described.

An injection method for determining interaction parameters between an analyte and a ligand in a biosensor is provided. In one example, the biosensor comprises a flow channel conduit in fluid communication with a flow cell conduit, said flow cell conduit housing at least a first sensing region and a second sensing region, said first sensing region having a ligand immobilized thereon and said second sensing region free of ligand. In this example, the injection method comprises obtaining a first fluid sample containing a reference material of a molecular weight and concentration sufficient to elicit a bulk refractive index response and obtaining a second fluid sample containing an analyte having a starting concentration. The first and second fluid samples are injected separately through the flow channel conduit under injection conditions that cause the reference material and analyte, respectively, to undergo a dispersion event in route to the flow cell conduit, wherein the dispersion event produces a concentration gradient. Although a sigmoidal profile is well suited for the present injection method, the injection conditions can be such that alternative concentration gradient profiles can be utilized. A first response is recorded at the second sensing region that represents the bulk refractive index response of the reference material thereby generating a standard curve. A reference diffusion coefficient is then determined for the reference material by fitting the standard curve to a dispersion model, wherein the dispersion model includes an apparent diffusion coefficient term. The reference diffusion coefficient is then multiplied by a calibration function to provide an effective diffusion coefficient specific for the analyte in the second fluid sample. The effective diffusion coefficient is incorporated into the dispersion model to represent the apparent diffusion coefficient term thereby providing a calibrated dispersion model. A second response at the first sensing region is recorded that represents an interaction between the analyte and the ligand as the second fluid sample progresses continuously through the flow cell conduit, wherein the second response provides a response curve. The interaction parameters between the analyte and ligand are determined by fitting an interaction model to the response curve, wherein the interaction model includes an analyte concentration term that is represented by the calibrated dispersion model.

In this example, the flow channel conduit may include a coiled section which is preferably vertically-oriented, wherein the flow channel conduit has a total volume from about 100 µl to about 200 µl. Furthermore, the injection conditions in this example may comprise a flow rate from about 100 µl/minute to about 200 µl/minute. In some instances, injection conditions are sufficient to yield a secondary tangential flow within the coiled section of the flow channel conduit.

A flow channel conduit configuration for use in a biosensing system is provided. In one instance, the flow channel conduit includes a first end portion connected to a first port of a valve. The flow channel conduit includes a coiled section oriented about a vertical axis. For example, the coiled section comprises a volume from about 50 µl to about 150 µl and preferably about 100 µl. In one example, the coiled section has an outer diameter from about 0.250 inches to about 0.50 inches and is preferably about 0.385 inches. However, an array of coiled configurations is possible when used in connection with the internal standard-based calibration method described herein and those dimensions described here should only be considered examples of suitable configurations. The flow channel conduit further comprises a second end portion extend from the coiled section and connected to a second port of the valve. Finally, a flow cell comprising at least one sensing region is in fluid communication with the second end portion of the flow channel conduit.

BRIEF DESCRIPTION OF THE DRAWINGS

FIG. 2 is a schematic illustration of a fluidic configuration in a biosensing system with the valve in the sample injection position.

FIG. 3 depicts a calibration curve expressed as an exponential decay of eight compounds of various molecular weight plotted against the effective diffusion coefficients generated from twenty-seven different experimental dispersion conditions.

FIG. 6A depicts the fitted response curves elicited using the rapid dispersion injection method for acetazolamide binding to immobilized carbonic anhydrase enzyme.

FIG. 6B depicts the fitted response curves elicited using the rapid dispersion injection method for CBS binding to immobilized carbonic anhydrase enzyme.

FIG. 6C depicts the fitted response curves elicited using the rapid dispersion injection method for furosemide binding to immobilized carbonic anhydrase enzyme.

DETAILED DESCRIPTION

Figure 1:
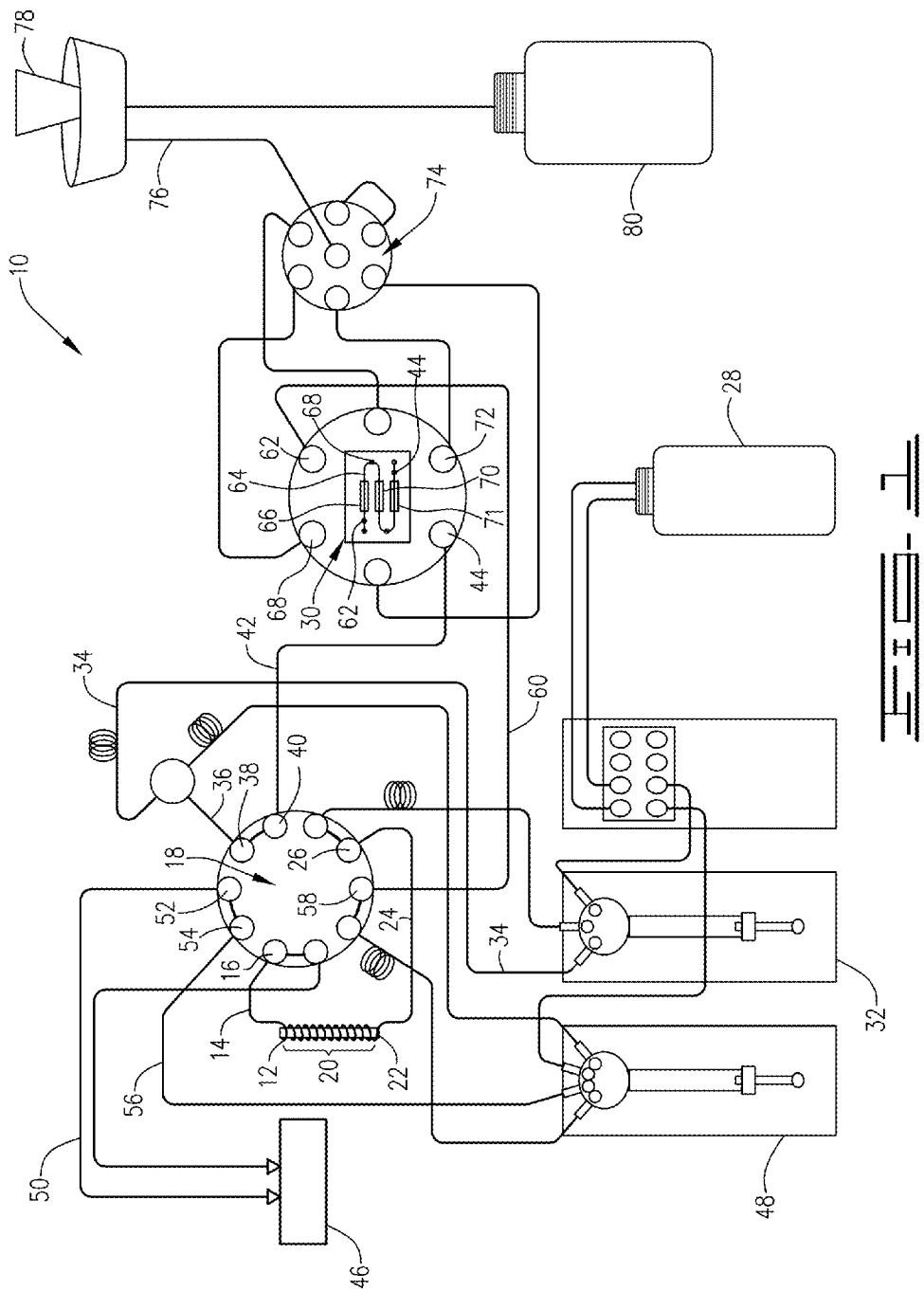
FIG. 1 is a schematic illustration of a fluidic configuration in a biosensing system with the valve in the sample load position.

The methods previously described in WO2012/087840 A1 (PCT/US11/65613), which is incorporated herein by reference in its entirety, related to a dispersion-based injection method (referred to herein as the "original dispersion injection method") that solved certain technical limitations of the prior art, namely the ability to accurately represent the analyte concentration in a dispersion-generated analyte concentration gradient from a single injection for label-free biomolecular interaction analysis.

Dispersion in a tube can be accurately modeled by Taylor's dispersion theory and, assuming that the initial concentration of analyte in a fluid sample is known, the theory provides an absolute method for determination of compound concentration at any time during the injection. As used herein, the term "dispersion" means a mixing process that causes the compound (e.g., analyte, reference material) concentration to become inhomogenous with respect to the cross-section and length of the flow channel conduit into which the fluid sample containing the compound is injected. Accordingly, a "dispersion event" is a dispersion produced by the particular injection conditions used in a particular assay. Dispersion is due to the combined action of analyte diffusion towards the walls of the capillary tube (also referred to herein as the "flow channel conduit" or "dispersion tube" or "tube") and the parabolic velocity profile within the capillary tube that results from convective flow through the capillary tube. Thus, the profile of an analyte concentration gradient created by dispersion is a complex function of the physical conditions present during the injection, such as temperature, applied forces (e.g. gravity), molecular weight, molecular shape, liquid viscosity, ionic strength, isoelectric point, flow channel geometry and flow rate. In biomolecular interaction analysis, an accurate representation of the analyte concentration is important since the binding interaction at the sensing region is influenced by the availability of analyte (i.e. analyte concentration). Accordingly, the actual analyte concentration gradient profile that passes over the sensing region contains information that defines the preceding analyte dispersion process and therefore becomes encoded or "imprinted" into the dependent analyte-ligand binding response curve.

The original dispersion injection method incorporates a relevant dispersion expression (also referred to herein as "dispersion term" or "dispersion model" or "dispersion equation") into the binding interaction model of interest to accurately define the analyte concentration at the sensing region as a function of time. Additionally, the original dispersion injection method involves the use of injection conditions that are sufficient to create a dispersion profile that is accurately represented by the dispersion term. An injection method that is performed under the physical conditions to comply with a particular dispersion theory, such as Taylor dispersion theory, not only provides an extended analyte concentration range, but also accounts for many physical parameters that affect dispersion such as the analyte diffusion coefficient. The inclusion of the analyte diffusion coefficient as a fitted parameter in the original dispersion injection method significantly extends biophysical characterization by label-free biosensors beyond what had been previously possible. In sum, the original dispersion injection method involves performing an analyte sample injection under physical conditions sufficient to cause the analyte to undergo a dispersion event that is in compliance with the assumptions and conditions under which the selected dispersion term is derived (such as Taylor dispersion theory). The original dispersion injection method is implemented without compromising other assay performance parameters such as throughput, robustness, reproducibility and resolution, although parameters can be modified if necessary for a particular assay.

However, the original dispersion injection method does place restrictions on certain injection conditions such as flow rate and tube volume. Generally, in order to conform to the Taylor dispersion model, the flow rate should remain low (e.g. 10-30 µl/min) and the tube volume should be quite large (e.g. 500 µl). In the interests of reducing sample volume and increasing effective flow rates, the present improved injection method (hereinafter "rapid dispersion injection method") utilizes coiled capillary tubes and the use of an internal standard to normalize the dispersion model for the coiling effect and increased flow rates. More specifically, the rapid dispersion injection method comprises the use of a flow channel conduit tightly wrapped about a vertically-oriented support in order to form a helical coil that permits the use of high flow rates and lower tube volumes.

However, the use of higher flow rates and tight coiling, among other factors, produces a dispersion that is significantly different than that which would be expected from the Taylor dispersion model utilized with the original dispersion injection method. At high flow rates in a flow channel conduit comprising a tight helical coil, strong tangential flow is produced due to centrifugal force. If the tangential flow is strong enough, the flow field within the flow channel conduit will split producing a secondary tangential flow such that the effective flow field resembles two adjacent tubular flows each with an effective diameter that is half that of the coil. This secondary tangential flow induces convective radial dispersion that augments diffusive radial dispersion producing an effective radial dispersion that more effectively counteracts convective axial dispersion. Lower effective axial dispersion allows shorter capillary tubes to be used at higher flow rates while preserving the sigmoidal form of the dispersion, which is conducive for model fitting.

A complete theory for quantitative prediction of a concentration gradient profile in a coiled tube does not exist. However, in coming to the present invention, it was envisaged that under these conditions (shorter capillary tubes with a tight coil at high flow rates), the diffusion coefficient of the analyte could be replaced by an effective diffusion coefficient that accounts for the effects of diffusion and the effect of the added dispersion caused by the axial convective flux which arises from the tangential centrifugal force generated as the liquid traverses the coiled dispersion tube. In some respects, this effective diffusion coefficient represents the dispersion process. In practice, combining the diffusion coefficient together with the accelerating effect of axial dispersion as an effective diffusion coefficient is equivalent to preserving the diffusion coefficient and then modifying the dispersion coefficient with a correction coefficient. Both approaches are equivalent in terms of calibration. It was found that an effective diffusion coefficient of an analyte could be estimated through the use of an internal standard and a calibration function. This effective diffusion coefficient can then be substituted into the Taylor dispersion model to provide a calibrated dispersion model. In doing so, the rapid dispersion injection method permits injection conditions that deviate from Taylor dispersion, but preserves the mathematical form of the dispersion process as it relates to the experimental conditions enabling a biophysically meaningful calibration model to be constructed. This rapid dispersion injection method provides an improvement over the previous dispersion injection by permitting significantly faster assay run times (due to the high flow rates and low volume) thereby increasing throughput without sacrificing the analytical benefits of the original dispersion injection method.

Additionally, the rapid dispersion injection method improves on the original dispersion injection method by providing a retention factor in the dispersion model which accounts for any reversible interactions of the analyte with the capillary tubing wall. The concentration of the compound ($C_t$) exiting the capillary tube increases in time and approaches the injected compound concentration ($C_0$) at the end of the injection. $C_t$ is equal to 0.5 $C_0$ at the residence time ($\tau$) for the capillary tube where t equals capillary volume (V) divided by flow rate (F). The results of dispersion are seemingly counterintuitive when first encountered because small molecules produce faster sigmoidal gradients and begin to elute after larger molecules. Referencing the essential mathematical results, it is helpful to conceptualize the process in the following manner. In the absence of tubing interactions, the average velocity of the soluble analyte molecules is equal to the average flow rate of the buffer (solvent). As the solvent front moves along the capillary it carries the compound at the same velocity. When a single volume of the capillary has been displaced the solvent front will be at $\tau$. The solvent front is the frame of reference for the dispersion process as the effects of diffusion and dispersion simply spread out the compound to either side of this moving boundary. The velocity field in the capillary tube is parabolic and is twice the average velocity at the center of the tube. The laminar streamlines near the capillary tube surface move very slowly due to wall drag while those near the center move relatively quickly. Small molecules have a high diffusion coefficient relative to large molecules and the diffusion process displaces them towards the walls and then away from the reflecting walls faster than the slower moving large molecules. Consequently a greater fraction of the low molecular weight ($M_r$) compound will be located in the slower moving streamlines close to the wall while a proportionally greater fraction of the high $M_r$ compounds will remain in the faster streamlines and hence will begin to emerge from the tube before the small molecules. Importantly the average elution time will be the same for both molecule populations as the population distribution of both is centered on the solvent moving boundary. At the residence time, the solvent boundary reaches the end of the capillary tube and the average cross-sectional concentration of both molecules will be exactly 50%. When a compound interacts reversibly with the tube walls, then the average velocity of the compound population will be retarded relative to the solvent front and this delay relative to the residence time is the retention factor (RF). In other words, the RF modifies the magnitude of the dispersion event to account for wall interactions.

For example, if a molecule in the liquid is highly soluble and does not interact with the wall of the capillary tube, then the retention factor is zero. This means that the average time taken for the molecule to reach the end of the capillary tube is the same as the buffer. However, if a molecule is less soluble, it may tend to stick to the wall. Microscopically, the molecule would adsorb onto the wall for a period of time before dissolving back into the liquid sweep along in the flow. If all the molecules in the sample react with the wall, then their arrival at the end of capillary tube will be delayed on average. This delay is the retention factor.

In an alternative embodiment, tubing wall interactions can be exploited to provide further functionality to the present method. In practice, unwanted tubing interactions are not generally observed and when present can be reduced by changing the composition of the solvent (i.e. buffer) in order to enhance the solubility of analyte. However, specific affinity binding interactions between the dispersing analyte and the tube wall can be incorporated intentionally by immobilizing a ligand to the wall of the dispersion tube. The resulting affinity interactions retard the progress of the analyte such that a specific affinity chromatographic-based separation is achieved in advance of arrival at the flow cell conduit. This may have broad utility in affinity characterization as impure samples can be used. Furthermore, the retarded analyte would become equilibrated into the running buffer as the sample buffer would move at a faster speed conferring a high tolerance to mismatches in sample buffer composition.

For example, mismatches in DMSO composition in the order of 0.1% (v/v) can interfere with binding responses obtained from evanescent field based detectors. This could be avoided by intentionally altering the dispersion tube wall to promote specific or non-specific reversible interactions. However, in this embodiment it is important to ensure that the tube wall area and separation time are sufficient to promote a significant retention factor thereby providing a well-resolved bulk sample buffer elution front that appears in the response curve in advance of the actual analyte. This may also be helpful in defining the residence time.

In one example, the rapid dispersion injection method is performed in a biosensor comprising a flow channel conduit that is in fluid connection with a flow cell conduit downstream from the analyte sample injection point. The flow channel conduit is tightly coiled around a vertically-oriented support and is preferably filled with a carrier fluid free of analyte prior to the analyte sample injection. Although it is preferred to use a vertically-oriented coil, it is not essential and other configurations are possible. The flow cell conduit houses at least two sensing regions, a first sensing region having one or more ligands immobilized on its surface and a second sensing region free of ligand. A first fluid sample comprising a reference material (e.g. sucrose) of sufficient molecular weight and concentration to elicit a bulk refractive index response is injected into the flow channel conduit under conditions sufficient to cause the reference material to undergo a dispersion event in route to the flow cell thereby producing a concentration gradient. Preferably, the concentration gradient possesses a sigmoidal profile; however other gradient profiles are possible. The bulk refractive index response of the reference material is recorded at the second sensing surface as the first fluid sample flows continuously through the flow cell thereby generating a standard curve. The standard curve provides an internal standard which acts as a witness to the particular injection conditions of that assay. The standard curve is then fitted to the dispersion model (Equations 2 and 3 described below) to calculate a reference diffusion coefficient. The reference diffusion coefficient is then multiplied by a calibration function (Equation 1 described below) to provide an effective diffusion coefficient. The calibration function is based in part on the molecular weight of the analyte to be tested such that the effective diffusion coefficient is specific for that particular analyte. The effective diffusion coefficient is incorporated into the dispersion model (Equations 2 and 3 below) and provides the apparent diffusion coefficient term (D') thereby providing a calibrated dispersion model.

Continuing with the current example, a second fluid sample comprising the particular analyte of interest is then injected under the same conditions as the first fluid sample containing the reference material. It should be understood that the second fluid containing analyte could be injected first or alternatively, the first fluid containing the reference material can be injected both before and after the second fluid. A second response at the first sensing region is then recorded and provides a response curve which represents the interaction between the analyte and the ligand as the second fluid progresses continuously through the flow cell conduit.

In this example, the retention factor is determined by comparing the residence time ($\tau$) for the first fluid with the residence time for the second fluid. For example, if the residence time for the first fluid is 100 seconds and the residence time for the second fluid is 110 seconds, the retention factor would be 110/100 or 1.1. The 1.1 value is then entered into the RF variable (Equation 3) in the dispersion model. Finally, the response curve is fit to a desired interaction model to determine the interaction parameters. The interaction model includes an analyte concentration term that is represented by the calibrated dispersion model (Equations 2 and 3, where D' is the effective diffusion coefficient determined from the internal standard and calibration function based on the molecular weight of the analyte being tested).

Thus, using the rapid dispersion injection method, the Taylor dispersion model can be used without being limited to the physical injection conditions that were previously required for compliance with Taylor theory under the original dispersion injection method. Specifically, high flow rates and low sample volumes can be utilized to decrease assay run times and preserve analyte sample. Additionally, the rapid dispersion injection method accounts for capillary wall interactions thereby providing a more accurate representation of the analyte concentration at the sensing region at any given time.

Referring now to FIGS. 1 and 2, an example of a fluidic configuration 10 of a biosensor for use in connection with the rapid dispersion injection method is depicted in the sample loading and injection phases, respectively. In FIG. 1 depicting the sample loading phase, flow channel conduit 12 is preferably pre-filled with a buffer fluid free of analyte. Flow channel conduit 12 comprises first end portion 14 in communication with port 16 of valve 18. Flow channel conduit 12 further comprises coiled section 20 which is coiled tightly around a vertically-oriented support structure 22. Flow channel conduit 12 further comprises second end portion 24 in communication with port 26 of valve 18. Buffer fluid from buffer source 28 is provided to flow cell 30 via pump 32 through buffer line 34 to line 36 to port 38 to port 40 to input line 42 to input port 44 of flow cell 30. As buffer flow is being supplied to flow cell 30, sample (either analyte sample or reference material sample) is loaded from sample rack 46 via pump 48 into line 50 through port 52 to port 54 to sample holding line 56. A small air bubble (not shown) can be provided if desired before loading sample to prevent buffer-sample dispersion in sample holding line 56 prior to injection.

Turning now to FIG. 2, the sample injection commences by switching valve 18 to injection orientation such that the initial analyte-buffer interface is formed at the junction between ports 54 and 16 of valve 18. Pump 48 drives the injection by pushing the sample through flow channel conduit 12 to port 26 to port 58 to flow cell input line 60 to flow cell port 62 and into flow cell conduit 64 over at least first sensing region 66 interrogated by a label-free transducer such as a surface plasmon resonance detector (not shown). Depending on the particular assay design, first sensing region 66 can be free of ligand such that if sample contains reference material (such as sucrose), the standard curve can be generated by recording the bulk refractive index response at first sensing region 66 and then exit at waste port 68. Additionally, waste port 68 can be closed and the sample can progress on to second sensing region 70 and third sensing region 71 is desired, where third sensing region is also free of ligand to provide a second standard curve. If the sample contains analyte, sample can progress on to second sensing region 70 which has ligand immobilized thereon to generate the response curve for the interaction between the analyte and ligand and then exit at waste port 72. It should be understood that the sensing regions in a flow cell can be configured such that each can be addressed independently of the other. As such, the term "first sensing region" and "second sensing region" and "third sensing region" should not be interpreted as providing any particular order along a flow cell conduit with respect to each other, but rather to denote separate sensing regions or separate portions of a common sensing region. Waste selector 74 allows for control of waste ports and transfers the tested sample through line 76 to wash station 78 and on to waste holding tank 80.

It should be understood that the lengths of the various lines and the position of the components with respect to each other in FIGS. 1 and 2 are not necessarily to scale and are provided in the manner depicted to illustrate an example of a fluidic configuration for a biosensing system suitable for use with the present method. One of skill in the art would understand that the components can be arranged with respect to each other in a number of configurations and the embodiment provided in FIGS. 1 and 2 is not limiting. As one example, a SensíQ Pioneer (Sensiq Technologies, Inc., Oklahoma City, Okla.) provides a suitable biosensing system to be used with the present methods. However, most biosensing systems could be retro-fitted to perform the present method by altering the flow channel conduit to provide suitable dispersion injection conditions.

The present rapid dispersion injection method has extended the original dispersion injection method through the discovery that the parameters that influence dispersion do not cause departures from the governing sigmoidal (or pulse) profile, but instead influence the time dependence of this profile. This allowed the general form of the Taylor dispersion model to be combined with a universal calibration function and an internal standard producing a general calibration that applies up to the limit where the form of the dispersion profile deviates significantly from Taylor's sigmoidal or pulse profile. More specifically, when expressed in dimensionless units, it was apparent that changing any of the dispersion parameters caused changes in dispersion that were essentially equivalent to apparent changes in the analyte diffusion coefficient which is proportional to the inverse cube root of the analyte molecular weight. It was therefore envisaged that a calibration relating the change in the apparent diffusion coefficient of analyte to its molecular weight could accurately account for changes in any given dispersion parameter by including an internal standard in addition to a standard calibration curve. The ratio of the measured apparent diffusion coefficient of the internal standard to its ideal diffusion coefficient from strictly Taylor dispersion conditions is a constant for all analytes other than a molecular weight component that remains. The internal standard represents a single molecular weight, but a universal relationship between molecular weight and this correction ratio was determined experimentally.

In brief, the universal calibration function was determined by measuring the bulk refractive index response of eight different compounds of varying molecular ($M_r$) under twenty-seven experimental dispersion conditions. This range of conditions included variation in temperature, flow rate, buffer composition and capillary tube geometry. An apparent diffusion coefficient (D') was obtained for the eight compounds by fitting the dispersion model defined by Equations 2 and 3 (set forth below) to each measured bulk refractive index response curve. These values were then divided by the apparent diffusion coefficient of an internal standard ($D'_0$) at each respective experimental condition and plotted as a function of analyte $M_r$. The internal standard in this experiment was sucrose which possesses a molecular weight equivalent to the average of the molecular weights of the eight calibration compounds which cover the relevant molecular weight range relevant in drug discovery. The dependence on molecular weight common to all dispersion conditions tested was defined as an exponential decay as shown in FIG. 3 thereby giving rise to the calibration function which is provided by Equation 1.

$$D'/D'_0 = (18.6277) * \exp(-1.3523 * \log[Mr]) + 0.3523 \qquad \text{Equation 1}$$

The dispersion model described herein is given in dimensionless form in order to reduce the mathematical complexity to its simplest form thereby enabling the mathematical relationships between the primary parameters to be readily observed. Additionally, the apparent diffusion coefficient (D') is substituted for the biophysical translational diffusion coefficient (D). It should be understood that the apparent diffusion coefficient (D') is also referred to herein as the "reference diffusion coefficient" with regards to the diffusion coefficient determined from the internal standard and the "effective diffusion coefficient" with regards to the calibrated diffusion coefficient for the target analyte generated from applying the calibration function to the reference diffusion coefficient in practice of the rapid dispersion injection method. Accordingly, the modified dispersion model in dimensionless form is for use with the present rapid dispersion injection methods and is represented by Equations 2 and 3:

$$\frac{C_t}{C_0} = \frac{1}{2} \cdot \left[ 2 - \mathrm{erf} \frac{1-\theta}{2\sqrt{\frac{k}{u \cdot L} \cdot \theta}} \right] \quad \text{Equation 2}$$

where $$k = \left[ \frac{u^2 \cdot d^2}{192 D'} + D' \right] \cdot (11 - 16 \cdot RF + 6 \cdot RF^2) \quad \text{Equation 3}$$

where
$C_t$=analyte concentration at detector (mol m$^{-3}$),
$C_0$=concentration of analyte injected (mol m$^{-3}$),
erf=Gauss error function,
k=effective dispersion coefficient,
$\theta$=dimensionless time=t/$\tau$,
$\tau$=mean analyte residence time (s)=V/u,
V=tube volume (m$^3$)
u=average velocity of fluid (m s$^{-1}$),
d=tubing diameter (m),
D'=compound apparent diffusion coefficient (m$^2$ s$^{-1}$)
RF=retention factor.

Figure 4A:
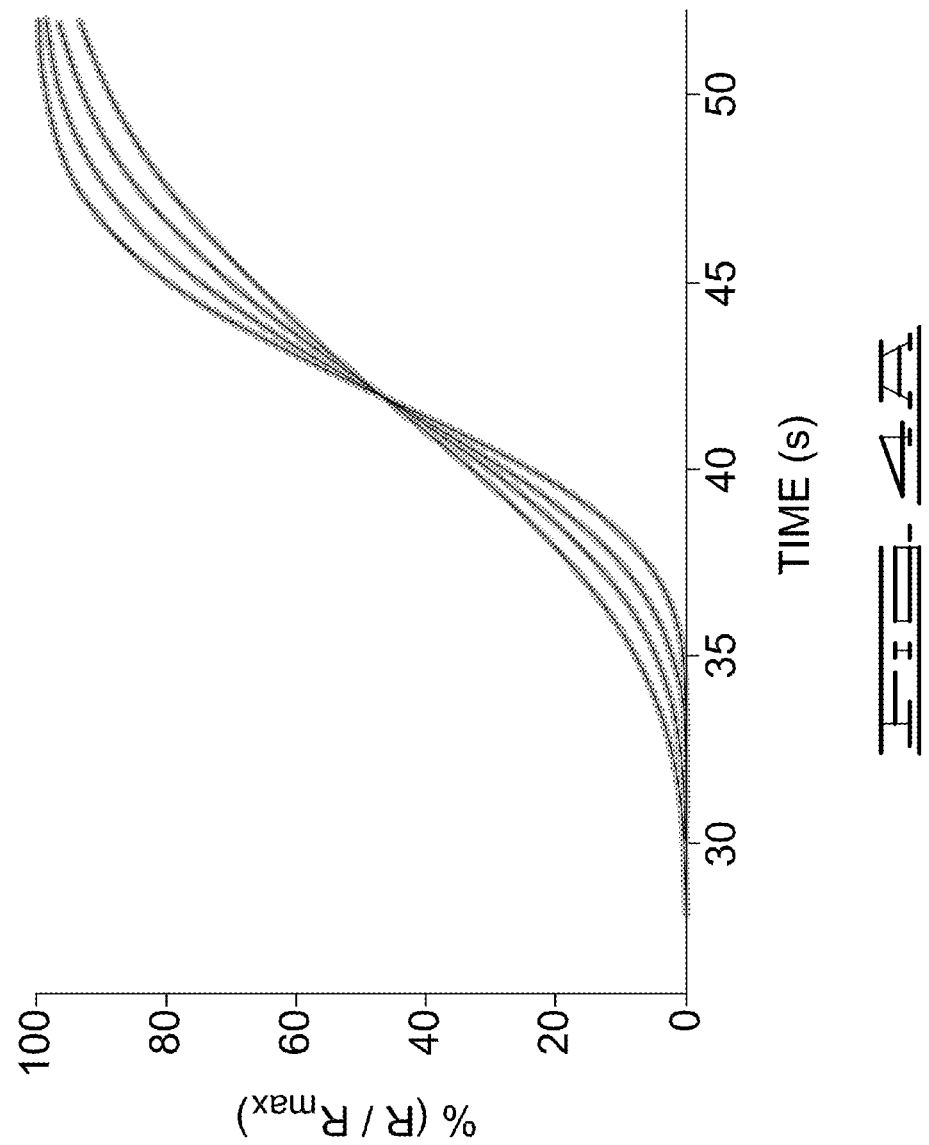
FIG. 4A depicts the refractive index response curves elicited from four compounds of varying molecular weight fitted to a dispersion model.
Figure 4:
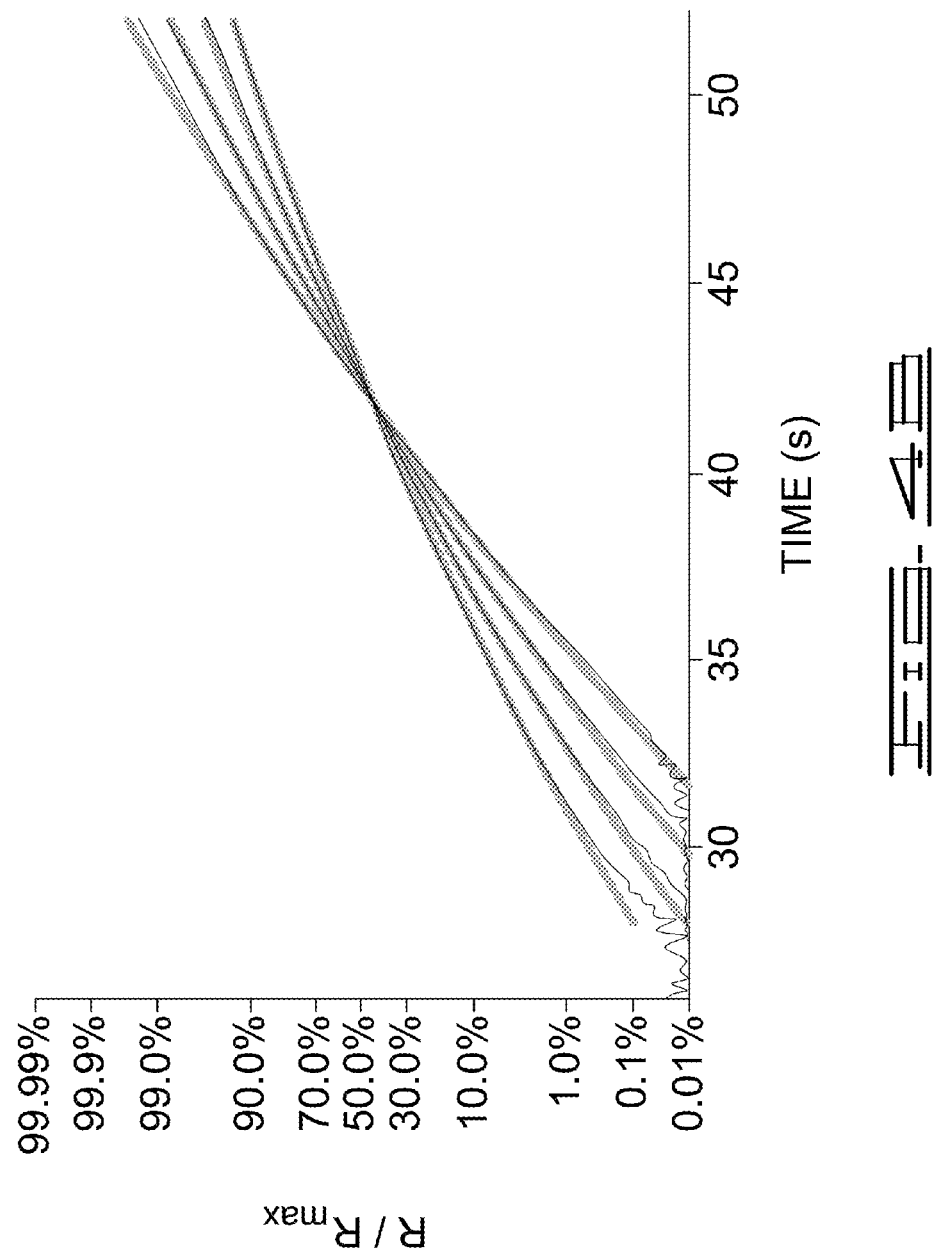
FIG. 4B is a representation of the data of FIG. 4a wherein the y-axis has been scaled according to a probability distribution about the mean.

A representative set of bulk refractive index dispersion curves (in triplicate) generated in the experiments to produce the calibration curve of FIG. 3 for one of the twenty-seven dispersion conditions tested is provided in FIGS. 4a and 4b. In FIGS. 4a and 4b, dimethylsulfoxide ($M_r$ 78 Da), glucose ($M_r$ 180 Da), sucrose ($M_r$ 342 Da) and nicotinamide adenine dinucleotide phosphate ($M_r$ 685), which represent three of the eight compounds used to generated the calibration curve and the internal standard (sucrose), were prepared at 1% (w/v) in standard HBS buffer. The dispersion conditions were as follows: temperature=25° C.; flow rate=150 µL/min; tube diameter=286 µm (approx. 0.010 inches); and tube volume=105.5 µL. The bulk refractive index was recorded for each in triplicate and the curves generated were normalized with respect to maximum bulk response for each curve and then fitted to the dispersion model (Equations 2 and 3). FIG. 4a shows the four dispersion curves distributed about the residence time (crossing point) (black lines) with increasing slope as a function of molecular weight. The four experimental curves appear perfectly superimposed upon the model curves (gray lines). FIG. 4b is a replicate plot of the data in FIG. 4a except that the y-axis has been scaled according to a probability distribution about the mean which tends to linearize the data and exaggerates the limits. This allows any slight departures from the model to be visualized. However, no departures from the model are evident as the experimental curves (black lines) remain perfectly aligned with the model curves (gray lines).

The data provided in FIGS. 4a and 4b represent an upper limit case near to a maximum flow rate where agreement with the model is assured over a $M_r$ range of 78-685 Da and a dilution range of three orders. Lower flow rates allow an extended $M_r$ and/or extended dilution range. In fact, the upper limit case shown above represents an extremely short sample contact time with ~25 seconds over the range, but is feasible given the 20 Hz data frequency (i.e. 500 response points over the dispersion range). Thus, the rapid dispersion injection method provides a significant improvement over assay run time as compared to previous injection methods.

In one embodiment, the volume of the flow cell conduit is small relative (<1%) to the flow channel conduit allowing dispersion within the flow cell conduit to be neglected when calculating the analyte concentration within the flow cell. If the volume of the flow cell conduit is significant (>1%) relative to the flow channel conduit, then the volume and geometry of the flow cell must be considered as an extension of the flow channel conduit when calculating the analyte concentration. In this case, the effective flow channel dispersion geometry includes terms that account for both the flow channel conduit geometry and the flow cell conduit geometry. Furthermore, the flow cell conduit may be part of the flow channel conduit where a defined boundary between these channels is absent. For example, the sensing regions may be disposed within the flow cell conduit itself where the flow channel geometry is consistent along its length. In practice the flow cell conduit is typically defined by a lower channel height in order to support high mass transport of analyte across the non-stirred boundary layer and onto the sensing surface. However, it is entirely possible to construct a flow channel conduit with a channel height that supports high mass transport rates. Lowering the height of the flow channel conduit would necessitate higher operating pressures, but would be expected to reduce the dispersion time. This may be appropriate where fast analysis of higher molecular weight analytes is required.

The embodiments described herein are described using a fluidic system where the various elements are connected in free space. For example, the flow channel conduit can be a capillary tube that is brought into fluid connection with a flow cell conduit using conventional free space adapters/fittings. However, it should be understood that the method can be performed using alternative designs wherein the flow channel conduit and flow cell conduit are integrated into a single miniature planar microfluidic device which offers practical advantages such as fabrication reproducibility. To this end, the internal standard-based calibration will automatically account for any changes in tube geometry.

In one aspect, the flow channel conduit is composed of a capillary tube of uniform circular cross-section and is drawn from an inert material such as PEEK, Teflon, Teflon derivatives, or glass, although other materials could be acceptable. The use of soft elastic materials which allows undesirable variation in geometry with respect to pressure (e.g. pump pulsation) should be avoided. However, in certain special case applications, the use of such compliant materials might be exploited to modulate the analyte dispersion profile. A more precise modulation of dispersion characteristics may be produced by making precise adjustments to the geometry of the flow channel conduit. Adjustment of the geometry may be performed on-the-fly as the dispersion is in progress or may be performed in advance of the dispersion injection. The volume of the dispersion tube dictates the amount of sample consumed and the rapid dispersion injection method can be practiced with dispersion tubes over a wide volume range due to the use of the internal standard-based calibration.

Just for purposes of example, the following injection conditions can be utilized in the present method. In one example, a flow channel conduit has a total volume of from about 100 µl to about 500 µl and more practically in the range of 100 µl to 150 µl and an inner diameter of about 0.005 inches to about 0.020 inches and more practically about 0.010 inches. In one example, the flow channel conduit comprises a coiled section that is vertically oriented. In this example, such as that depicted in FIGS. 1 and 2, flow channel conduit 12 is wrapped around a vertically-oriented support structure, where support structure 22 has a diameter of approximately 0.265 inches. If flow channel conduit having an inner diameter of 0.010 inches is used, then the outer diameter of the coil 20 is approximately 0.285 inches and in this particular example, coiled section 20 has a volume of about 100 µl. Flow rates from about 10 µl/min to about 200 µl/min can be used and more practically in the range of 100 to 150 µl/min, but this parameter is often dependent on the volume and diameter of the tube, the presence of a coil (which allows for the higher end flow rates) and the limits of the pumps used in the biosensor system. It should be noted that lower tube diameters may result in back-pressure whereas higher diameter tubes may not conform to the desired sigmoidal profile. Flow rates can be decreased to solve issues with back-pressure, however, this will decrease assay speed. Nonetheless, due to the internal standard-based calibration described herein, a wide range of injection conditions can be utilized in conjunction with the present method that are not included in the exemplary injection conditions provided above.

As described in WO2012/087840 A1, a sigmoidal-type dispersion injection or pulse-type dispersion injection can be used with the current rapid dispersion injection method. However, for use with the present method, the flow channel conduit preferably contains a coiled section and the internal standard-based calibration (Equation 1) should be used in connection with Equations 2 and 3 herein for the sigmoidal injection, and Equation 4 (below with Equation 3 for k) for the pulse injection method. However, the preferred sample volume to flow channel conduit ratios previously described for use with the pulse method (preferably sample volume of <5% of the flow channel conduit capacity volume) and sigmoidal method (preferably sample volume of >50% of the flow channel conduit capacity volume) are still applicable.

$$C(t) = \frac{2C_{in}V_i}{\pi^{3/2}d^2\sqrt{kt}} \exp\left[-\frac{0.25L^2(1-t/\tau)^2}{kt}\right]$$ Equation 4 where
$C(t)$=analyte concentration at detector (mol m$^{-3}$)
$C_{in}$=concentration of analyte injected (mol m$^{-3}$)
$V_i$=sample injection volume (m$^3$)
d=capillary (flow channel conduit) diameter (m)
$\tau$=mean analyte residence time (s) or L/u
L=length of capillary (m)
u=average velocity of fluid (m s$^{-1}$)
k=Taylor-Aris Apparent dispersion coefficient (m$^2$ s$^{-1}$) which is represented by Equation 3:
Note that the dispersion coefficient (k) is the same as that required for sigmoidal dispersion, but the mathematical form of the dispersion changes from a sigmoidal approach of a fixed maximum to a Gaussian-like peak of varying width and height.

The sigmoidal injection and pulse injection embodiments are each capable of generating smoothly varying analyte concentration gradients over 3-4 orders in magnitude which is suitable for label-free biosensing. However, the maximum concentration of analyte in the pulse injection approach is significantly less than the analyte concentration in the initial sample (neat analyte concentration) while the maximum concentration of analyte in the sigmoidal injection approach is equal to the neat analyte concentration.

In practice of the rapid dispersion injection method, all injection parameter conditions that produce an essentially sigmoidal-shaped dispersion profile (requires sample volume typically more than half dispersion tube volume) or peak-shaped dispersion profile (obtained from a low sample volume, or pulse) are compatible with the universal, internal standard-based calibration described herein. However, certain parameter combinations may tend to linearize the sigmoidal dispersion. For example a high molecular weight (<1000 Da) and low residence time (<30 s) may produce such curves. These curves are influenced primarily by convective flow because the rate of diffusion is not sufficient to cause diffusive dispersion. This class of dispersion can be modeled with a polynomial function and has no molecular weight dependence. In this case, a high molecular weight internal standard is employed to generate the calibration function. Therefore, this second calibration function is molecular weight independent and can be employed when the dispersion profile is found to deviate from sigmoidal profiles.

A similar approach can be alternatively adopted for pulse dispersion gradients. Certainly if flow rate is reduced, then high molecular weight analytes can produce sigmoidal dispersion profiles albeit at the expense of decreasing the flow rate. In this instance, it may be desirable to choose a flow channel conduit volume/diameter and operating pressure that minimizes sample consumption for a given analyte class (e.g. proteins, drugs, particles) while providing adequate throughput. Therefore the second molecular weight-independent polynomial is a more appropriate option.

A flow channel conduit can be actively heated or cooled to modify the analyte dispersion. The use of varying temperatures can also provide thermodynamic analysis of interactions. Thermal denaturation of the reagents can limit these temperature based methods. Typically, protein-based analytes can tolerate temperatures that do not exceed 50° C. However, even among protein-based analytes there are exceptions to this limit. Drug like molecules, nucleic acids, and carbohydrate-based analytes are far more stable allowing temperatures to approach the boiling point of the carrier buffer (typically approximately 100° C. at atmospheric pressure). Higher operating pressures enable even higher temperatures to be applied. Cryogenic agents such as glycerol can be added to the carrier fluid (i.e. sample buffer) to prevent freezing at lower temperatures. Therefore the absolute temperature range can be stated as any temperature where the carrier stream does not boil or freeze at the operating pressure within the flow channel conduit.

In one aspect, the flow cell conduit is typically a rectangular compartment with a high numerical aperture where the volume and height of the flow cell channel is minimized. In one example, the flow cell is rectangular with approximate dimensions of length=3 mm, width=0.5 mm and height=30 µm. However, other more complex geometries can be chosen in the practice of the dispersion method.

The pump used in connection with the current method should preferably provide pulse-free, pressure driven flow where variation in flow rate and pressure are minimal as this facilitates accurate modeling of the dispersion process. Syringe pumps are suitable, although peristaltic pumps may be adequate where absolute accuracy is not required.

In one aspect, the sensing regions are interrogated optically by a surface-sensitive refractometer based on surface plasmon resonance (SPR). Similar performance can be expected when using these surface sensitive evanescent-field based refractometers. Other optical detection principles such as interferometry are less sensitive to bulk refractive index and more specific to the mass loading event that manifests as a growing biofilm layer. These detectors are advantageous where interference from bulk refractive is undesirable. In practice SPR's sensitivity to both bulk refractive index and surface refractive index is advantageous as it is possible to verify dispersion parameters from the bulk refractive index response independently of the specific binding response. For example, analyte present at high concentrations often provides a bulk refractive index response that is adequate to determine the analyte diffusion coefficient and general dispersion parameters thereby allowing these parameters to be fitted as constants when applying the affinity model to the specific binding response curve. Alternative placement of the sensing regions such as at intervals along the flow channel conduit enable replicates of the same affinity interaction to be performed under different dispersion conditions providing a more comprehensive analysis of dispersion-dependent binding. When an analyte stream enters the flow cell conduit, binding to ligand immobilized at the sensing region will occur. This mass loading increases the average refractive index close to the sensing surface that is probed by the evanescent field. The evanescent field is created from the reflection of a wedge-shaped monochromatic beam (where the light source is an 880 nm light emitting diode) from the surface under conditions of total internal reflection. This results in a reflection minimum with respect to incidence angle when a thin noble metal film is present at the interface. Alternatively, a wavelength-dependent reflection minimum can be generated using a fixed angle polychromatic light source optical configuration. In both cases, the metal is preferably gold due to its stability and ease by which it can be made to anchor biocompatible films or hydrogels that are suitable for affinity binding studies. The position of the reflectance minimum changes with changes in surface refractive index and are tracked using a photodiode array and a minimum hunt algorithm that provides a real-time location of the minimum. The detector is pre-calibrated to convert this real time location to an equivalent refractive index change which is then plotted as a function of time to create a real-time binding curve.

Various binding interaction models can be used in conjunction with the dispersion methods described herein. In one example, the two-compartment 1:1 pseudo-first-order kinetic interaction model is utilized. This model is composed of two differential equations that describe the change in the concentration of affinity complexes (dR/dt) at a sensing region and the analyte concentration gradient (dC/dt) as the analyte passes from the bulk carrier liquid through the diffusion boundary layer within the flow cell conduit onto the sensing region.

$$\frac{dC}{dt} = (-k_a C(R_{max} - R) + k_d R + k_m(C_{in} - C)) \quad \text{Equation 5}$$

$$\frac{dR}{dt} = k_a C(R_{max} - R) - k_d R \quad \text{Equation 6}$$

where
R=biosensor response (response units (RU)),
$R_{max}$=maximum response expected if all ligand sites are occupied (RU)
$C_{in}$=injected analyte concentration (M), which becomes zero when the dissociation phase begins.
C=concentration of the analyte at the sensing surface (M)
$k_m$=mass transport constant (RU $M^{-1}$ $s^{-1}$)
$k_a$=association rate constant ($m^{-1}$ $s^{-1}$)
$k_d$=dissociation rate constant ($s^{-1}$).

$k_m$ can be a fitted parameter or alternatively can be estimated from the following equation (assuming that the use of dextran hydrogel does not contribute to mass transport limitations):

$$k_m = 10^9 \cdot M_r \cdot 1.43 \cdot \left[ \frac{1 - \left(\frac{L_1}{L_2}\right)^{2/3}}{1 - \left(\frac{L_1}{L_2}\right)} \right] \cdot \sqrt[3]{\frac{D^2 \cdot F}{H^2 \cdot W \cdot L_2}} \quad \text{Equation 7}$$

where
F=flow rate ($m^3$ $s^{-1}$)
$L_1$ and $L_2$=lengths (m) of the functionalized surface relative to the start and end of the sensing region, respectively
H=height (m) of the flow cell conduit
W=width (m) of the flow cell conduit.

Under preferred conditions, the geometry of the flow cell is well defined, allowing these parameters to be held constant. The analyte molecular weight ($M_r$) is usually known or alternatively it can be estimated from D. However fitting $k_m$ rather than pre-calculating it is often preferable with little loss in the quality of the fit.

In the present method, the concentration of analyte in the flow as a function of time depends on the dispersion process which is given by the aforementioned equations (Equations 2 and 3 and Equations 4 and 3). The appropriate equation is substituted into the chosen binding interaction model.

In the pulse injection embodiment, it is appropriate to represent $C_{in}$ in the binding interaction model with the dispersion term provided in Equation 4 and 3 upon calibration using the internal standard and determination of the effective diffusion coefficient D'. In the sigmoidal injection embodiment, it is appropriate to represent $C_{in}$ in the binding interaction model with the dispersion term provided in Equations 2 and 3 upon calibration using the internal standard and determination of the effective diffusion coefficient D'. In either embodiment, $C_{in}$ is specified as a function of time. Thus, $k_a$, $k_d$, $R_{max}$, $k_m$, are fitted model parameters and D' is pre-calculated and entered as a constant using the internal standard-based calibration (with Equation 1) described herein. Alternatively, D' can be fitted, but this would require two or more binding response curves to ensure accuracy. If multiple analyte species exist in the injected sample, then the appropriate dispersion term is included as a separate term for each dispersed species. In many cases, mass transport limitation is negligible, where $C_{in}=C$, and the two-compartment 1:1 kinetic interaction model reduces to the simple "rapid mixing" model by eliminating Equation 7 and is commonly referred to as 1:1 pseudo-first-order kinetic interaction model. These kinetic models have many variations that account for deviations from the assumption of a 1:1 interaction. For example a ligand with more than one analyte binding site requires a heterogeneous analyte kinetic interaction model. If the analyte possesses more than one binding site for the ligand then a heterogeneous ligand interaction model can be applied. If the formation of binding complexes proceed through the formation of a short lived intermediate complex, then a kinetic interaction with conformational change model can be chosen. If a large population of different analyte species co-exist, where each possesses different binding properties to the immobilized ligand, then an analyte distribution model can be chosen. Similarly, a distribution model can be applied when a large population of ligand species exist (i.e. ligand distribution model). The distribution model assumes that a large population of analyte species, or ligand species, co-exist and distribution analysis methods are applied in the fit to generate a probability distribution of the affinity space (i.e. plot of $k_a$ versus $K_D$, $k_d$ versus $K_D$) constructed from fitting a set of binding interaction curves. Each of the above models can be simplified when the influence of kinetic rate constants are minimal thereby reducing each to a simple affinity analysis.

Using the current method, any of the above interaction models of interest can be appropriately modified to incorporate a dispersion term. For example, a two-site binding interaction model can be chosen where the response recorded by the biosensor ($R_{(t)}$) is given by the sum of multiple components as represented by the following:

$$R_{(t)} = AB + AB_2 + RI_{analyte} \qquad \text{Equation 8}$$

with fitted parameters $k_a$, $k_{a2}$, $k_d$, $k_{d2}$, $R_{max}$, $R_{max2}$, and D, $D_{solvent}$.

In Equation 8, AB and $AB_2$ are the response components due to affinity complexes formed between the analyte at two independent analyte binding sites. A similar approach can be used to represent a multisite interaction model where more interaction sites exist. Each binding component can include affinity and/or kinetic parameters as appropriate to the data set to be analyzed. To express each binding component as a kinetic model, a separate set of binding rate equations (Equations 5 and 6) are required for each binding component. $RI_{analyte}$ is the bulk refractive index term associated with the analyte and is defined by Equations 4 and 3 when running pulse injections or Equations 2 and 3 when running sigmoidal injections. This bulk refractive index term is required because refractive index based detector for label-free biosensing measure all contributions to refractive index change and includes surface mass loading, but also bulk refractive index changes. An additional bulk refractive index term for any solvent mismatch may be defined by the appropriate Taylor dispersion equations with the addition of a solvent diffusion coefficient ($D'_{solvent}$). In the case of high analyte retention, there will be a significant difference between the residence time for the dispersion tube and the retention time allowing significant separation of both bulk solvent dispersion from the analyte dispersion thereby improving the reliability of curve fitting to interaction models.

Additionally, a multi-site affinity interaction model that assumes a rapid approach to steady-state (i.e. kinetic terms not required) can also be employed. The three-site version of a multisite affinity model can be expressed as:

$$R_{eq} = [R_{max1} * C/(K_{D1}+C)] + [R_{max2} * C/(K_{D2}+C)] + [R_{max3} * C/(K_{D3}+C)] \qquad \text{Equation 9}$$

The equilibrium response ($R_{eq}$) is the sum of three affinity binding terms each defined by independent parameter values for the saturation response ($R_{max}$) and affinity constant ($K_D$). However, this affinity model cannot be fitted directly to the real-time Dispersion injection binding response curve. Therefore, a real-time affinity isotherm model is used (Equation 10 below) that is analogous to Equation 9, but where $R_{eq}$ was expressed as a function of injection time ($R_{eq(t)}$) allowing the isotherm model to be fitted directly to the dispersion injection curve.

$$R_{eq(t)} = R_{max1} * C_{(t)}/(K_{D1}+C_{(t)}) + R_{max2} * C_{(t)}/(K_{D2}+C_{(t)}) + R_{max3} * C_{(t)}/(K_{D3}+C_{(t)}) \qquad \text{Equation 10}$$

In Equation 10, $C_{(t)}$ is given by the appropriate dispersion term (Equations 4 and 3 for pulse injections and Equations 2 and 3 for sigmoidal injections). Since this affinity model is complex, it is preferable to use two or more dispersion injection curves in order to constrain fitted parameters globally for improved performance. The benefit of global model fitting is the added information content that results from including two binding curves recorded under different conditions. Performing dispersion injection at two different neat concentrations is a simple approach, but does require a second analyte sample of different neat concentration be added to the sample rack. To avoid having to prepare analyte dilutions, it is possible to obtain two curves under significantly different conditions by changing the dispersion conditions and not the neat analyte concentration. For example, replicate dispersion injections performed at different injection flow rates produce different Taylor dispersion profiles. The two dispersion injection binding response curves are offset with respect to time because $\tau$ is a function of flow rate, but they are readily fitted with a binding interaction model where one or more parameters are constrained globally. In one aspect, the binding interaction constants and the diffusion coefficient are fitted globally while $\tau$ would be fitted locally. This approach can be applied generically to the wide range of binding interaction models available. Furthermore binding interaction models may still be fitted to sub-regions for each curve in the curve set for global model fitting. However, when time is limiting, it is possible to obtain reliable parameter values from fits to single curves providing higher throughput.

There are a variety of additional aspects that can be used in connection with the injection methods described herein. In one aspect, a soluble ligand that interacts with the analyte is added to the injected fluid sample. This causes a fraction of the analyte to be bound in bulk solution and unavailable for binding to the ligand at the sensing surface. The degree to which binding of analyte to the ligand at the sensing surface is reduced is dependent on the affinity of the analyte for the second soluble ligand in solution. This allows competitive models to be used to calculate the affinity or kinetic parameters for solution phase binding events. Dispersion injections can be used to generate a continuous dose response in the soluble ligand while holding the analyte concentration constant thereby allowing a complete competitive affinity analysis from a single dispersion injection. It should be understood that the binding interaction model need not represent any biophysical binding interaction process itself. In fact, a phenomenological binding interaction model that can account for some of the interaction properties can be utilized. Alternatively, an arbitrary mathematical model with a set of parameters that are completely unrelated to the actual interaction parameters can often suffice when kinetic constants and affinity are not required. However, these models may also be adapted to include a dispersion term. Hence, the dispersion process and the associated diffusion coefficients may be estimated. The arbitrary models can fit to data that cannot be defined by conventional biophysical models, but can act as calibration curves for relating a response to other assay parameters of interest.

It should be noted that while the above methods do enable indirect measurement of the analyte diffusion coefficient from fitted dispersion terms embedded in binding interaction models, these should be considered approximate since they are not measured directly. Diffusion coefficients measured from fitting the dispersion function directly to a bulk refractive index response curve are reliable. Apparent diffusion coefficients obtained from either type of analysis may be converted to approximate translational diffusion coefficients (effective diffusion coefficient) by again using the internal standard. For example, the diffusion coefficient for the internal standard is first determined under full Taylor dispersion conditions and this is then expressed as a ratio with the apparent diffusion coefficient measured under the coiled dispersion tube/rapid flow conditions. This ratio can then be normalized for molecular weight using the universal calibration (Equation 1).

In order to illustrate various aspects of the methods described above, the following Example is provided. It should be understood that various modifications could be applied without departing from the scope of the invention as described in the appended claims. As such, the Examples should not be construed to limit the present invention.

EXAMPLE

The purpose of the present example is to determine the interaction parameters for three sulfonamide inhibitors (acetazolamide ($M_r$ 222 Da), 4-carboxybenzenesulfonamide (CBS) ($M_r$ 201 Da), and furosemide ($M_r$ 330 Da)) binding immobilized carbonic anhydrase enzyme using the present rapid dispersion injection method and the standard fixed concentration injection (FCI) method.

Materials and Methods

A SensíQ Pioneer instrument (Sensiq Technologies, Inc., Oklahoma City, Okla.) was the biosensing system used in this example. For the FCI method, the flow channel conduit was omitted so that the volume from the injector valve to the flow cell was <3 µL thereby reducing any dispersion such that each dilution concentration can be assumed approximately constant over the course of the injection. For the FCI method, two-fold serial dilutions of acetazolamide (500 nM to 31.25 nM), CBS (15 µM to 0.938 µM), and furosemide (40 µM to 1.25 µM) were separately prepared in running buffer (Hepes buffered saline with 0.005% Tween-20 and 5% DMSO). Each dilution was separately injected for 2 min followed by dissociation for 4 min without regeneration. All injections were performed at 25° C.

For the rapid dispersion injection method, the flow channel conduit comprised an inner diameter of 0.010 inches, a total volume of 105 µl, a vertically-oriented coiled section having a volume of 100 µl, and a coil outer diameter of 0.390 inches. The flow rate for the rapid dispersion injections was 50 µL/min. The following test solutions were prepared in running buffer (Hepes buffered saline with 0.005% Tween-20 and 5% DMSO) at the indicated starting (neat) concentration: furosemide (40 µM); CBS (30 µM); and acetazolamide (1 µM). 3% (w/v) sucrose dissolved in the running buffer (Hepes buffered saline with 0.005% Tween-20 and 5% DMSO) was used as the internal standard for the rapid dispersion injections. All injections were performed at 25° C.

Curve fitting to kinetic interaction curves was performed using Qdat, a simulation and curve-fitting package based on the Scrubber data analysis software developed by BioLogic Software, Inc., (Campbell, Australia). Qdat was employed for double referencing of all data sets. The Qdat software uses numerical integration of the binding rate equations to generate simulations and fit interaction models to interaction curves using standard Levenberg-Marquardt optimization. The standard kinetic 1:1 interaction model was used for both the FCI assay and the rapid dispersion injection assays. The dispersion terms (Equations 2 and 3) were included as the appropriate concentration variable when fitting all dispersion injection data to the interaction model and the dispersion terms were calibrated based on the internal-standard based calibration method using Equation 1 as described herein for each analyte tested.

Results

Figure 5A:
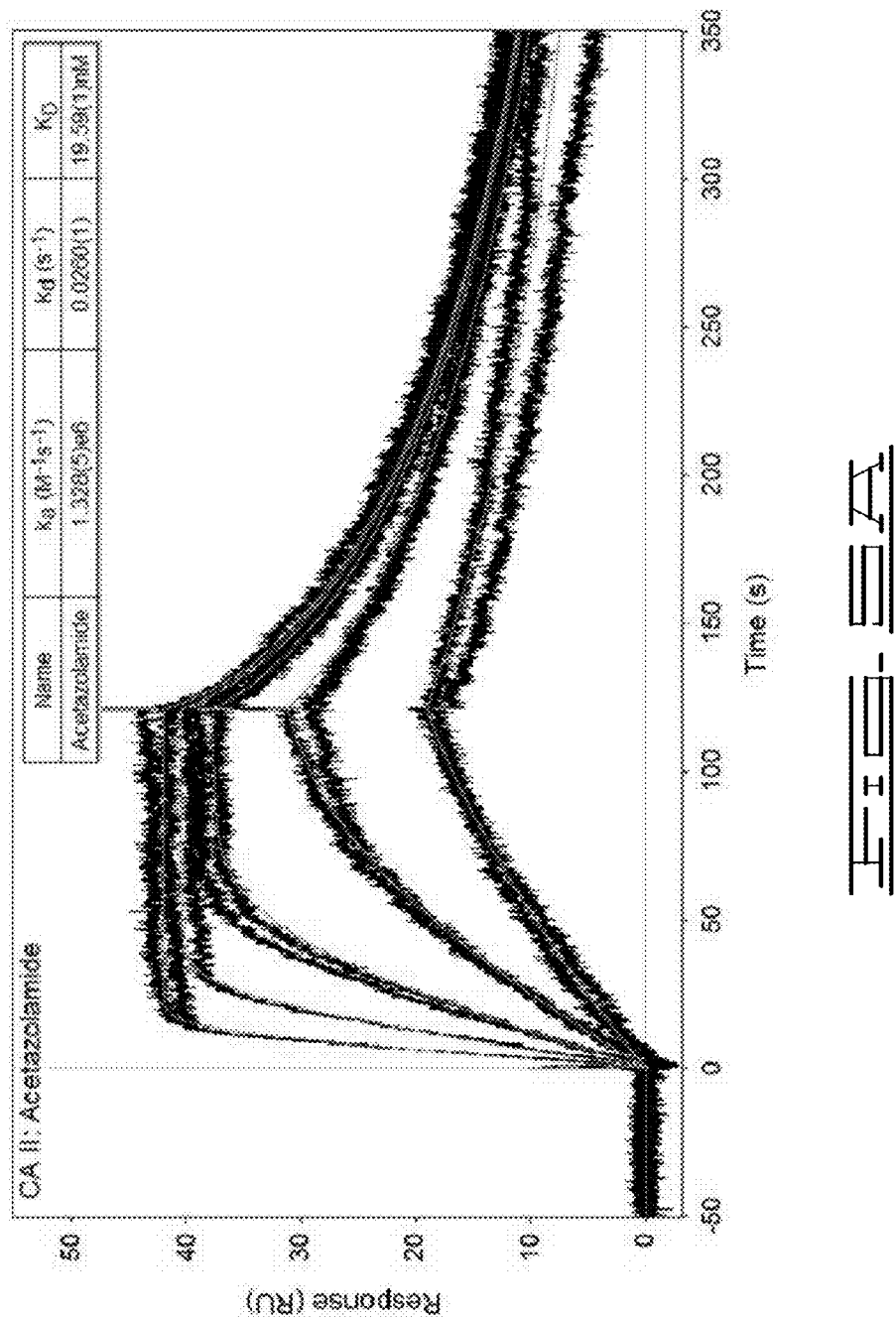
FIG. 5A depicts the fitted response curves elicited using the standard fixed concentration injection method for a two-fold serial dilution of acetazolamide binding to immobilized carbonic anhydrase enzyme.
Figure 5B:
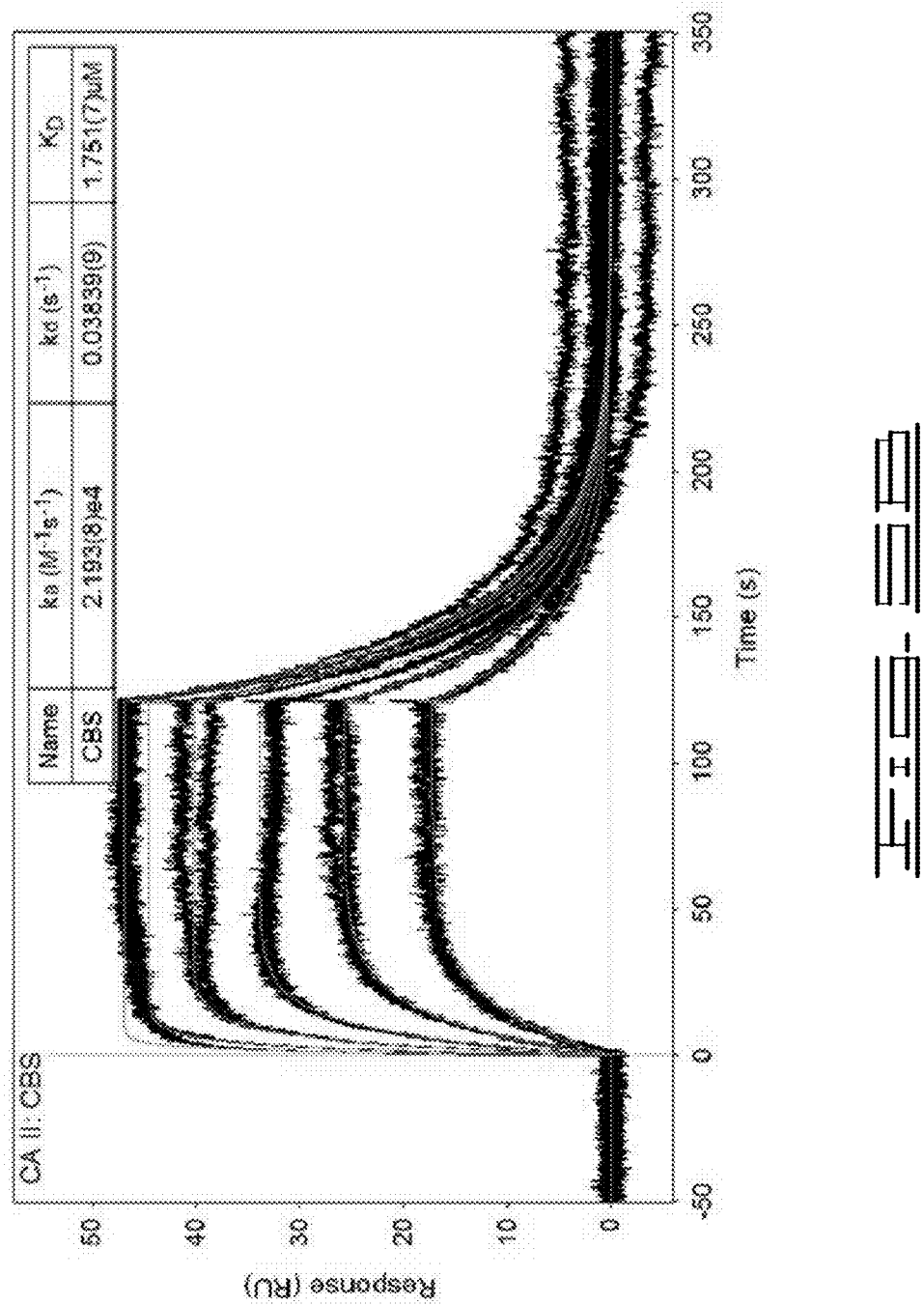
FIG. 5B depicts the fitted response curves elicited using the standard fixed concentration injection method for a two-fold serial dilution of 4-carboxybenzenesulfonamide (CBS) binding to immobilized carbonic anhydrase enzyme.
Figure 5C:
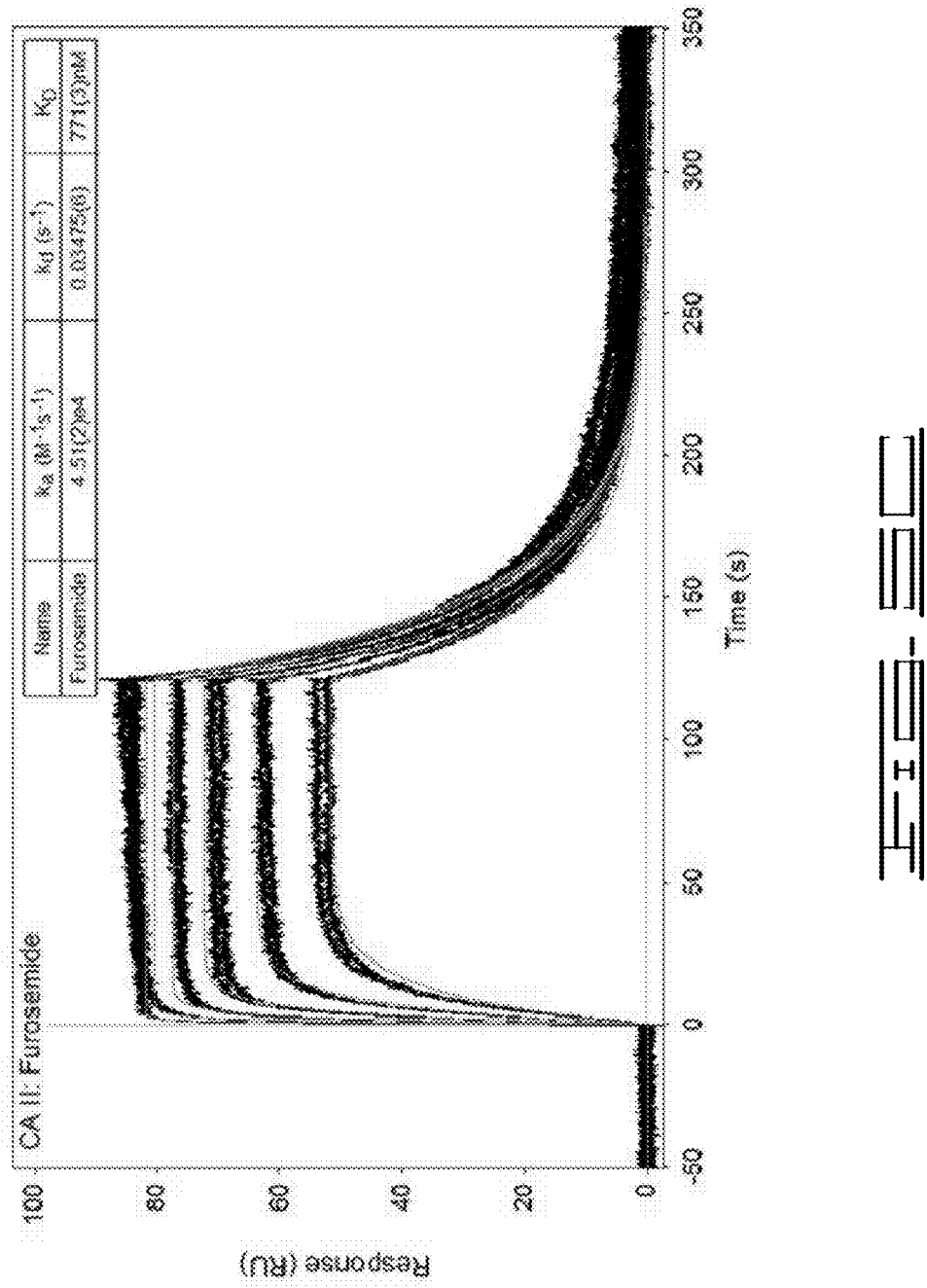
FIG. 5C depicts the fitted response curves elicited using the standard fixed concentration injection method for a two-fold serial dilution of furosemide binding to immobilized carbonic anhydrase enzyme.
Figure 5A:
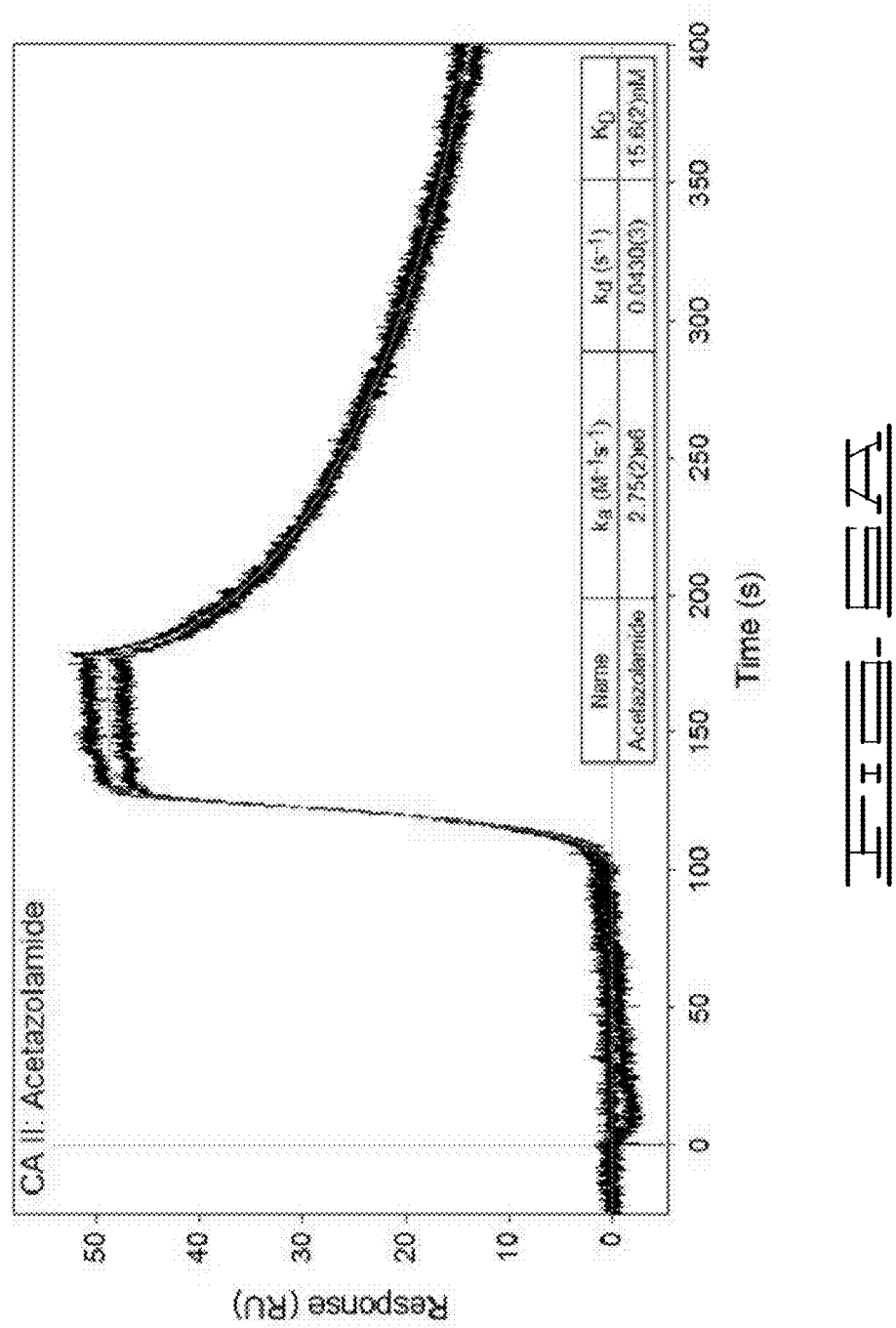

FIGS. 5A, 5B, and 5C depict the fitted response curves elicited using the FCI method for acetazolamide, CBS, and furosemide, respectively. Table 1 below represents the kinetic rate constants for the three analytes tested using the FCI method.

TABLE 1

Kinetic rate constants obtained from FCI assay

| Analyte | $k_m$ ($s^{-1}$) | $k_a$ ($M^{-1}s^{-1}$) | $k_d$ ($s^{-1}$) | Rmax (RU) | KD | Res SD (RU) |
|---|---|---|---|---|---|---|
| Acetazolamide | 7.708(7)e6 | 1.328(5)e6 | 0.0260(1) | 43.582(7) | 19.59(1) nM | 1.167 |
| CBS | 5.00E+08 | 2.193(8)e4 | 0.03839(9) | 49.66(4) | 1.751(7) uM | 1.597 |
| Furosemide | 5.00E+08 | 4.51(2)e4 | 0.03475(6) | 83.45(5) | 771(3) nM | 2.551 |

FIGS. 6A, 6B, and 6C depict the fitted response curves elicited using the rapid dispersion injection method for acetazolamide, CBS, and furosemide, respectively. Table 2 below provides the kinetic rate constants, the apparent diffusion coefficient for each analyte ($D_{app}$)(also referred to as the "effective diffusion coefficient") and number of aggregates ($N_{ag}$)(where 1 indicates an assumed monomer) for the three analytes tested using the rapid dispersion injection method.

TABLE 2

Kinetic rate constants obtained from rapid dispersion injection method

| Analyte | $k_m$ ($s^{-1}$) | $k_a$ ($M^{-1}s^{-1}$) | $k_d$ ($s^{-1}$) | Rmax (RU) | KD | Res SD (RU) | $D_{app}$ ($m^2s^{-1}$) | $N_{ag}$ |
|---|---|---|---|---|---|---|---|---|
| ACZ | 9.13(1)e6 | 2.75(2)e6 | 0.0430(3) | 49.499(9) | 15.6(2) nM | 0.978 | 9.67E-10 | 1 |
| CBS | 5.00E+08 | 1.972(6)e4 | 0.03299(4) | 52.79(3) | 1.673(5) uM | 2.23 | 1.01E-09 | 1 |
| Furo | 5.00E+08 | 4.580(7)e4 | 0.04207(3) | 83.28(2) | 918(1) nM | 1.737 | 8.29E-10 | 1 |

Thus, the present invention is well adapted to carry out the objects and attain the ends and advantages mentioned above as well as those inherent therein. While preferred embodiments of the method have been described for the purpose of this disclosure, changes in the particular types of dispersions created and the associated dispersion terms can be made by those skilled in the art, and such changes are encompassed within the spirit of this invention as defined by the appended claims. As used in the appended claims, the terms "Equation 1", "Equation 2", "Equation 3", "Equation 4", "Equation 5", "Equation 6", "Equation 7", "Equation 8", "Equation 9", and "Equation 10" are defined by the corresponding equations provided in the specification.

What is claimed is:

1. An injection method for determining interaction parameters between an analyte and a ligand in a biosensor, the biosensor comprising a flow channel conduit, said flow channel conduit having a coiled section, said flow channel conduit in fluid communication with a flow cell conduit, said flow cell conduit housing at least a first sensing region and a second sensing region, said first sensing region having said ligand immobilized thereon and said second sensing region free of ligand, the method comprising the steps of:
   obtaining a first fluid sample containing a reference material of a molecular weight and concentration sufficient to elicit a bulk refractive index response;
   obtaining a second fluid sample containing said analyte having a starting concentration;
   injecting the first fluid sample and separately injecting the second fluid sample through the flow channel conduit at a flow rate of about 10 µl/min to about 200 µl/min under injection conditions that cause the first fluid sample and the second fluid sample to undergo similar dispersion events en route to the flow cell conduit, wherein passage of said first fluid sample through said coiled section results in said dispersion event of said first fluid sample and produces a concentration gradient of said reference material and wherein passage of said second fluid sample through said coiled section results in said dispersion event of said second fluid sample and produces a concentration gradient of said analyte;
   recording a first response at the second sensing region that represents the bulk refractive index response of the reference material in the first fluid sample thereby generating a standard curve;
   recording a second response at the first sensing region that represents an interaction between the analyte and the ligand as the second fluid sample progresses continuously through the flow cell conduit, wherein the second response provides a response curve;
   calculating a reference diffusion coefficient for the reference material by fitting the standard curve to a dispersion model, wherein the dispersion model includes an apparent diffusion coefficient term and the dispersion model is represented by Equation 2 and Equation 3;
   determining an effective diffusion coefficient for the analyte by multiplying the reference diffusion coefficient by a calibration function, said calibration function represented by Equation 1;
   incorporating the effective diffusion coefficient into the dispersion model to represent the apparent diffusion coefficient term thereby providing a calibrated dispersion model; and
   determining the interaction parameters between the analyte and ligand by fitting an interaction model to the response curve, wherein the interaction model includes an analyte concentration term that is represented by the calibrated dispersion model.

2. The injection method of claim 1 wherein the concentration gradient possesses a sigmoidal profile.

3. The injection method of claim 1 wherein the first fluid sample is injected before the second fluid sample.

4. The injection method of claim 1 wherein the coiled section is vertically-oriented.

5. The injection method of claim 1 wherein the injection conditions comprise a flow rate of 150 µl/minute.

6. The injection method of claim 5 wherein the coiled section has a total volume of approximately 105.5 µl.

7. The injection method of claim 1 wherein the flow channel conduit includes a coiled section oriented vertically and the injection conditions include a flow rate sufficient to yield a secondary tangential flow within the coiled section.

8. The injection method of claim 1 wherein the first fluid sample is injected before the second fluid sample.

9. The injection method of claim 1 wherein the reference material is sucrose.

10. An injection method for determining interaction parameters between an analyte and a ligand in a biosensor, the biosensor comprising a flow channel conduit, said flow channel conduit having a coiled section, said flow channel conduit in fluid communication with a flow cell conduit, said flow cell conduit housing at least a first sensing region and a second sensing region, said first sensing region having said ligand immobilized thereon and said second sensing region free of ligand, the method comprising the steps of:
   obtaining a first fluid sample containing a reference material of a molecular weight and concentration sufficient to elicit a bulk refractive index response;
   obtaining a second fluid sample containing said analyte having a starting concentration;
   injecting the first fluid sample and separately injecting the second fluid sample through the flow channel conduit at a flow rate of about 10 µl/min to about 200 µl/min under injection conditions that cause the first fluid sample and the second fluid sample to undergo similar dispersion events en route to the flow cell conduit, wherein passage of said first fluid sample through said coiled section results in said dispersion event of said first fluid sample and produces a concentration gradient of said reference material and wherein passage of said second fluid sample through said coiled section results in said dispersion event of said second fluid sample and produces a concentration gradient of said analyte;
   recording a first response at the second sensing region that represents the bulk refractive index response of the reference material in the first fluid sample thereby generating a standard curve;
   recording a second response at the first sensing region that represents an interaction between the analyte and the ligand as the second fluid sample progresses continuously through the flow cell conduit, wherein the second response provides a response curve;
   calculating a reference diffusion coefficient for the reference material by fitting the standard curve to a dispersion model, wherein the dispersion model includes an apparent diffusion coefficient term and the dispersion model is represented by Equation 3 and Equation 4;
   determining an effective diffusion coefficient for the analyte by multiplying the reference diffusion coefficient by a calibration function, said calibration function represented by Equation 1;
   incorporating the effective diffusion coefficient into the dispersion model to represent the apparent diffusion coefficient term thereby providing a calibrated dispersion model; and
   determining the interaction parameters between the analyte and ligand by fitting an interaction model to the response curve, wherein the interaction model includes an analyte concentration term that is represented by the calibrated dispersion model.

11. The injection method of claim 10, wherein the coiled section is vertically-oriented.

12. The injection method of claim 10, wherein the injection conditions comprise a flow rate of 150 µl/minute.

13. The injection method of claim 10, wherein the flow channel conduit includes a coiled section oriented vertically and the injection conditions include a flow rate sufficient to yield a secondary tangential flow within the coiled section.

* * * * *